(12) United States Patent
Hemerly et al.

(10) Patent No.: US 10,647,988 B2
(45) Date of Patent: May 12, 2020

(54) METHOD FOR PROMOTING AN INCREASE IN PLANT BIOMASS, PRODUCTIVITY AND DROUGHT RESISTANCE

(71) Applicant: Universidade Federal Do Rio De Janeiro, Cidade Universitária-Ilha do Fundão (BR)

(72) Inventors: Adriana Silva Hemerly, Leblon (BR); Carinne de Nazaré Monteiro Costa, Rio de Janeiro (BR); Luiz Mors Cabral, Ghent (BE); Vanessa Costa Lurif, Niterói (BR); Paulo Cavalcanti Gomes Ferreira, Leblon (BR)

(73) Assignee: Universidade Federal Do Rio De Janeiro, Cidade Universitaria-Ilha do Fundao (BR)

( * ) Notice: Subject to any disclaimer, the term of this patent is extended or adjusted under 35 U.S.C. 154(b) by 90 days.

(21) Appl. No.: 15/064,435

(22) Filed: Mar. 8, 2016

(65) Prior Publication Data
US 2016/0177327 A1 Jun. 23, 2016

Related U.S. Application Data

(63) Continuation-in-part of application No. PCT/BR2015/000024, filed on Mar. 2, 2015.

(30) Foreign Application Priority Data

Feb. 28, 2014 (BR) .......................... 1020140048812

(51) Int. Cl.
C12N 15/82 (2006.01)
C07K 14/415 (2006.01)

(52) U.S. Cl.
CPC ........ *C12N 15/8218* (2013.01); *C07K 14/415* (2013.01); *C12N 15/8261* (2013.01); *C12N 15/8273* (2013.01)

(58) Field of Classification Search
None
See application file for complete search history.

(56) References Cited

U.S. PATENT DOCUMENTS

| | | | |
|---|---|---|---|
| 5,034,323 A | 7/1991 | Jorgensen et al. | |
| 5,107,065 A | 4/1992 | Shewmaker et al. | |
| 5,283,184 A | 2/1994 | Jorgensen et al. | |
| 5,453,566 A | 9/1995 | Shewmaker et al. | |
| 5,759,829 A | 6/1998 | Shewmaker et al. | |
| 5,942,657 A | 8/1999 | Bird et al. | |
| 2003/0175965 A1 | 9/2003 | Lowe et al. | |
| 2003/0180945 A1 | 9/2003 | Wang et al. | |
| 2008/0213871 A1 | 9/2008 | Sticklen | |
| 2009/0265815 A1* | 10/2009 | Alexandrov | C07K 14/415 800/298 |
| 2010/0170007 A1 | 7/2010 | Bielenberg et al. | |
| 2012/0198585 A1* | 8/2012 | Xiao | C12N 15/8218 800/279 |
| 2014/0283215 A1 | 9/2014 | Steffens | |
| 2017/0037426 A1* | 2/2017 | Alexandrov | C07K 14/415 |

FOREIGN PATENT DOCUMENTS

| | | |
|---|---|---|
| EP | 2295582 A2 | 3/2011 |
| EP | 2391642 A2 | 12/2011 |
| WO | 2004029257 A1 | 4/2004 |
| WO | 2006105106 A2 | 10/2006 |
| WO | 2011130815 A2 | 10/2011 |
| WO | 2015127521 A1 | 9/2015 |

OTHER PUBLICATIONS

Zhou et al. (Plant Physiol., June 162(2):1030-1040; Published Jun. 2013; first published on line May 8, 2013).*
Alonso et al. (Science, 301:653-657, 2003).*
Joseph Ecker (Germplasm / Stock: SALK¬_022332 Submitted and available on public domain on Aug. 9, 2002).*
Arziman et al. (Nucleic Acids Research, 33:582-588, 2005).*
Emery et al. (Current Biology 13:1768-1774, 2003).*
Colliver et al. (Plant molecular Biology, 35:509-522, 1997).*
Elomaa et al. (Molecular Breeding, 2:41-50, 1996).*
Bruening (Proc. Natl. Acad. Sci., 95:13349-13351, 1998).*
Gutterson (HortScience 30:964-966,1995).*
Masuda, H.P. et al.: "ABAP1 is a novel plant Armadillo BTB protein involved in DNA replication and transcription." EMBO J. 27:2746-2756, 2008.
Zhou, X.F. et al.: "CYCLIN H;1 regulates drought stress responses and blue light-induced stomatal opening by inhibiting reactive oxygen species accumulation in *Arabidopsis*." Plant Physiology, 162:1030-1041, 2013.
PCT International Search Report, PCT/BR2015/000024, dated Jul. 9, 2015.
PCT International Written Opinion, PCT/BR2015/000024, dated Jul. 9, 2015.
Zuker et al., Modification of flower color and fragrance by antisense suppression of the flavanone 3-hydroxylase gene, (2002) Molecular Breeding 9: 33-41.
Younis et al., RNA Interference (RNAi) Induced Gene Silencing: A Promising Approach of Hi Tech Plant Breeding, (2014) Int. J. Biol. Sci. 10: 1150-1158.
Waterhouse and Helliwell, Exploring Plant Genomes by RNA-Induced Gene Silencing, (2003) Nat. Rev. Genet. 4:29-38.
Verma and Dwivedi, Lignin genetic engineering for improvement of wood quality: Applications in paper and textile industries, fodder and bioenergy production, (2014) South African Journal of Botany 9: 107-125.

(Continued)

*Primary Examiner* — Vinod Kumar
(74) *Attorney, Agent, or Firm* — TraskBritt

(57) ABSTRACT

Described are methods for promoting increase in plant biomass and yield. This increase has its visible effects in organs such as leaf, stem, root and production of fruits and seeds. Further described is the increase in tolerance of those plants to drought, generating plants better adapted to the environmental changes, improving their growth, biomass and yield.

3 Claims, 12 Drawing Sheets

Specification includes a Sequence Listing.

(56) References Cited

OTHER PUBLICATIONS

Toppino et al., Reversible male sterility in eggplant (*Solanum melongena* L.) by artificial micro-RNA-mediated silencing of general transcription factor genes, (2011) Plant Biotechnology Journal 9: 684-692.

Shimada et al., Increase of amylose content of sweetpotato starch by RNA interference of the starch branching enzyme II gene (IbSBEII), (2006) Plant Biotechnology 23, 85-90.

Ralph et al., NMR characterization of altered lignins extracted from tobacco plants down-regulated for lignification enzymes cinnamyl-alcohol dehydrogenase and cinnamoyl-CoA reductase, (1998) Proc. Natl. Acad. Sci. USA 95: 12803-12808.

Mansoor et al., Engineering novel traits in plants through RNA interference, (2006) Trends in Plant Science 11: 559-565.

Liu et al., High-Stearic and High-Oleic Cottonseed Oils Produced by Hairpin RNA-Mediated Post-Transcriptional Gene Silencing, (2002) Plant Physiol. 129:1732-1743.

Kasai and Kanazawa, RNA silencing as a tool to uncover gene function and engineer novel traits in soybean, (2012) Breeding Science 61: 468-479.

Jorgensen et al., Chalcone synthase cosuppression phenotypes in petunia flowers: comparison of sense vs. antisense constructs and single-copy vs. complex T-DNA sequences (1996) Plant Mol. Biol. 31:957-973.

Bhaskar et al., Suppression of the Vacuolar Invertase Gene Prevents Cold-Induced Sweetening in Potato, (2010) Plant Physiology 154: 939-948.

Belide et al., Modification of seed oil composition in *Arabidopsis* by artificial microRNA-mediated gene silencing, (2012) Frontiers in Plant Science 3, 168, 6 pages.

Ali et al., RNA interference in designing transgenic crops, (2010) GM Crops 1:4, 207-213.

\* cited by examiner

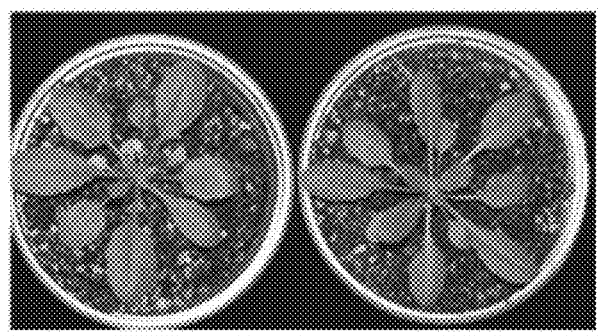
FIG. 3A
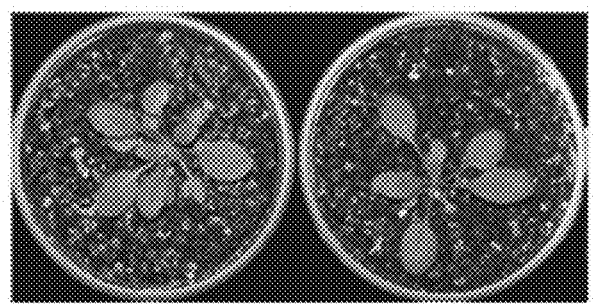
FIG. 3B
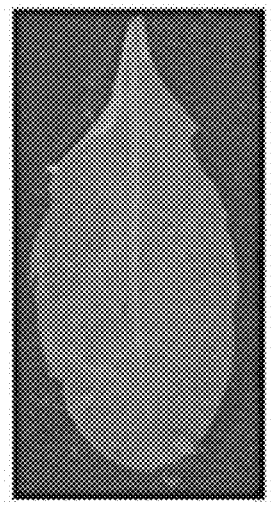
FIG. 3C
FIG. 3D
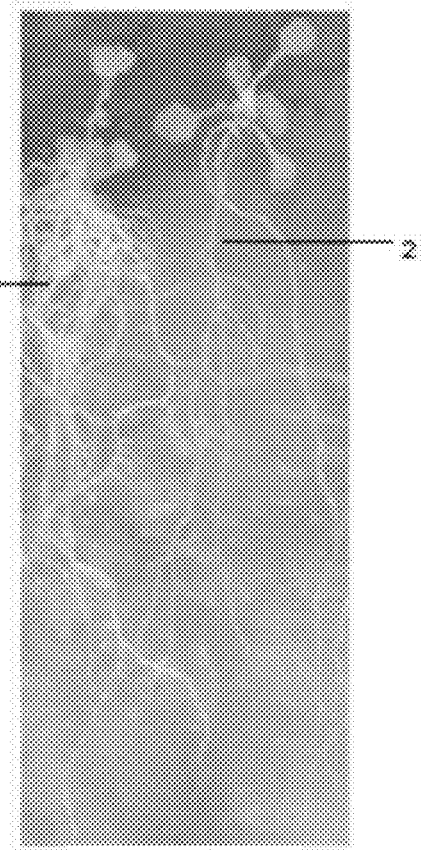
FIG. 3E

FIG. 5A  FIG. 5B

Days after germination (DAG)

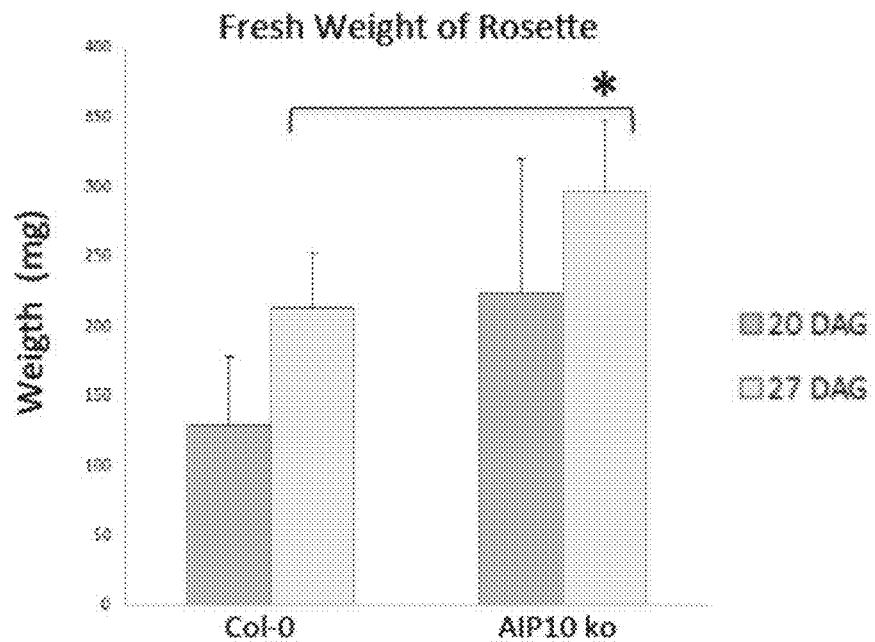
FIG. 8A
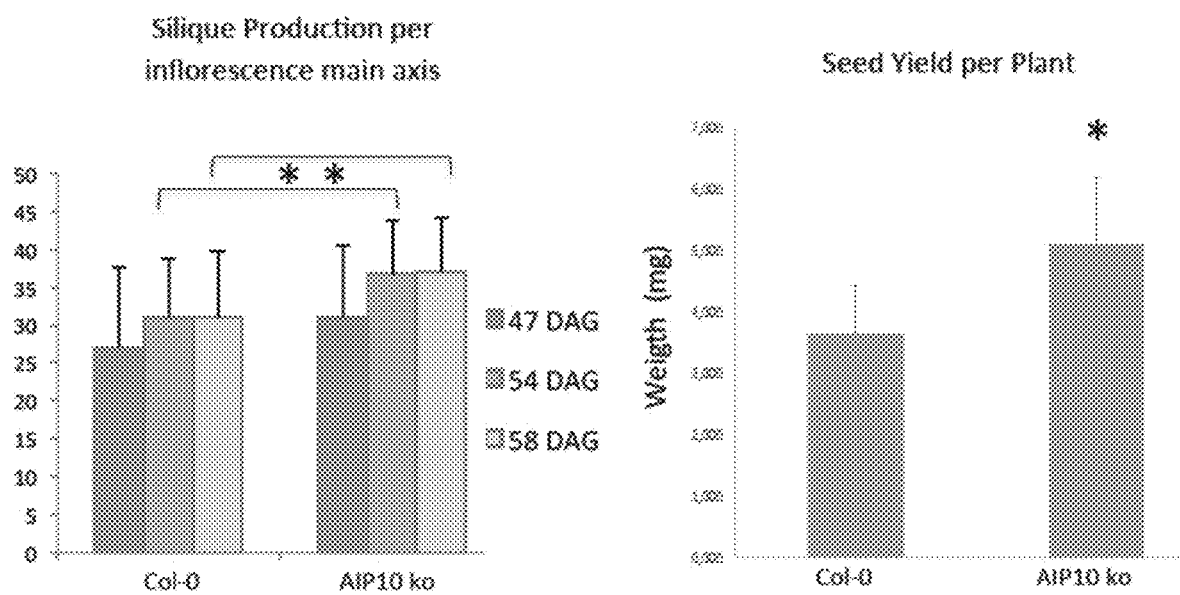
FIG. 8B
FIG. 8C

METHOD FOR PROMOTING AN INCREASE IN PLANT BIOMASS, PRODUCTIVITY AND DROUGHT RESISTANCE

PRIORITY CLAIM

This application is a continuation-in-part of pending International Patent Application PCT/BR2015/000024, filed Mar. 2, 2015, designating the United States of America and published as International Patent Publication WO 2015/127521 A1 on Sep. 3, 2015, which claims the benefit under Article 8 of the Patent Cooperation Treaty to Brazilian Patent Application Serial No. BR1020140048812, filed Feb. 28, 2014, the disclosure of each of which is hereby incorporated herein in its entirety by this reference.

TECHNICAL FIELD

This application relates to biotechnology generally, and particularly to a method for promoting an increase in plant growth as a whole, leading, e.g., to an increase of biomass and seed yield and associated plants, progeny and, e.g., seeds. This increase has its visible effects in plant organs such as leaf, stem, roots, and in fruit production. Furthermore, the method is capable of increasing tolerance of the treated plants to drought.

BACKGROUND

The increasing world population has led to a rising demand for food, energy, and natural resources. Food production is closely related to water availability. Water, once available in much of the earth's surface, is the limiting factor in agricultural productivity. Thus, the steady increase of agriculture, together with climate change, is making the use of water resources unsustainable. In this scenario, a need exists to increase agricultural productivity in a sustainable manner, that is, to produce more using less water (Morison et al., 2008; FAO, 2012). Another problem to be faced is the availability of areas for cultivation because, increasingly, these areas are scarce and a great concern exists for the conservation and preservation of biodiversity.

Many efforts are being made to reduce the amount of water used for agriculture, and to produce "more by drop" and per hectare. One way to achieve that increased agricultural productivity can be through plant breeding. In such a way, it is possible to increase yield, but also minimize losses by biotic and abiotic stresses (Morison et al., 2008; Parry and Hawkesford, 2012).

However, to improve plant growth, intervention in the cell cycle of the plant is often needed. As it is well known, the cell cycle is a conserved and critical step in the life cycle of eukaryotic organisms where the genetic material from the mother cell is duplicated and divided between two daughter cells. This process is coordinated with changes in the architecture of the cell and has four well-defined stages: the stage of synthesis, mitosis and two intervals, known as gap1 (G1) and gap2 (G2).

In the synthesis phase (S phase), the DNA is replicated to produce copies of the two daughter cells. During the G2 gap, new proteins are synthesized and the cell doubles in size. Later, in mitosis (M phase), the replicated chromosomes are separated so that each daughter cell receives a copy.

In the interval between mitosis and DNA synthesis phase (G1 gap), nuclear DNA is prepared for replication.

Errors in this cycle progression could have serious consequences for the integrity of the genome and, therefore, for the development of the organism. Thus, to ensure that the events occur properly and the DNA is duplicated only once, the cells have checkpoints between transitions (Ramires-Parra et al., 2005; Berkmans and de Veylder, 2009; de Veylder et al., 2007).

The first checkpoint determines whether the cell enters the DNA synthesis phase (G1) or remains in the quiescent state. The first step of the DNA synthesis phase is the formation of a structure that will regulate the entire process of cell division, the pre-replicative complex (pre-RC) (Machida et al., 2005; M. I. Aladjem, 2007).

The first step in the formation of the pre-RC is the recognition of DNA replication origins by the Origin Recognition Complex (ORC). After this recognition, the CDC6 and CDT1 proteins join the ORC complex and will recruit the MCM complex, which has helicase activity, culminating in the licensing of DNA for replication (Machida et al., 2005; Blow and Dutta, 2005; Sun and Kong, 2010).

It was revealed in an article by our group (H. P. Masuda, L. M. Cabral, L. De Veylder, M. Tanurdzic, J. De Almeira Engler, D. Geelen, D. Inze, R. A. Martienssen, P. A. Ferreira, and A. S. Hemerly—ABAP1 is a novel plant protein armadillo BTB involved in DNA replication and transcription, EMBO Journal, 2008), that *Arabidopsis thaliana* has a new cell cycle regulation mechanism in which the ABAP1 protein plays a central role. This protein interacts with members of the DNA replication machinery, transcription factors and other classes of proteins (Masuda et al., 2008). One of these proteins with which ABAP1 interacts was called AIP10. Knockout plants for AIP10 gene have larger roots and leaves, produce more seeds and have greater resistance to water stress situations.

Other research and disclosures have also been made to promote increased plant biomass, however, by different methods. For example, International Application WO 2011/130815, the contents of which are incorporated herein by this reference, discloses a method for increasing plant biomass by introducing a polynucleotide sequence into the plant genome.

Through the use of recombinant DNA, in the patent application EP2295582, the contents of which are incorporated herein by this reference, the inventor seeks the enhancement of plant specimens by controlling nucleic acid expression of CDC27A. The disclosure described in the application WO 2004/029257, the contents of which are incorporated herein by this reference, seeks to alter the development of a plant.

The patent EP2391642, the contents of which are incorporated herein by this reference, refers to a protein complex that promotes plant growth. More specifically, the disclosure relates to the use of specific proteins of the anaphase-promoting complex/cyclosome to increase plant growth rates and/or enhance cell division rates. The above-mentioned application further relates to a method for improving the growth of plants by overexpression of APC10 gene and/or its variants or repression of the SAMBA gene and/or its variants. The genes whose activities are changed in patent application EP2391642 are distinct and regulate, in cell cycle, processes other than those presented herein.

BRIEF SUMMARY

The plants, techniques, and methodology described herein are capable of promoting an increase in the growth of a plant as a whole, leading to an increase of biomass and seed yield, the effects being visible in organs such as leaf, stem, root, and fruit production. In parallel, also provided are methods and means of increasing plant drought tolerance, generating plants better adapted to the environmental changes, improving their growth, biomass and yield.

Described herein is methodology to regulate cell cycle rates by modulating the expression of the gene that produces the AIP10 protein, which participates in the ABAP1 regulatory network that is composed by members of the DNA replication machinery, transcription factors and other classes of proteins, so that there is an increase in plant biomass and plant yield. Furthermore, the modulation of AIP10 levels also increases tolerance of plants to drought.

Meanwhile, the incorporated EP Patent Application EP 2391642 relates to a process for increasing plant growth by overexpression of the gene APC10, which is a subunit of the APC/C complex and which, in turn, is one of the mitotic cycle regulators. Furthermore, the above-mentioned patent application describes a method of plant growth through suppression of the gene that produces the SAMBA protein, which is a protein that regulates the activity of APC10 protein, which is not addressed herein.

Moreover, none of the disclosures cited reached the same positive results in increasing seed productivity, enlarged organs such as leaf, stem, root, fruit production as well as increased drought tolerance, as described herein.

BRIEF DESCRIPTION OF THE FIGURES

FIG. 1 shows the PCR results with the use of specific primers for genomic DNA (LP—left primer, and RP—right primer) and the T-DNA (LB—left border), respectively. Size 1000 by corresponds to the DNA amplification of the wild-type Col0-0 plant, and 800 bp corresponds to the AIP10 knockout gene with the T-DNA insertion.

FIGS. 3A-3E show images of leaves, rosettes and roots of AIP10 knockout (AIP10ko) and wild-type Col0-0 plants. FIG. 3A shows top views of the development of rosette and leaves of two AIP10ko plants. FIG. 3B shows top views of the development of rosette and leaves of two wild-type Col0-0 plants. FIG. 3C shows a top view of a leaf sample collected in one of the two AIP10ko plant samples (from FIG. 3A) that is representative of the average leaf size in these plants. FIG. 3D shows a top view of a leaf sample collected in one of the two wild-type plant samples (from FIG. 3B) that is representative of the average leaf size in these plants. FIG. 3E shows the phenotypic difference in the root development of AIP10ko (1) and wild-type Col0-0 plants (2).

FIG. 4A shows an image of 11-day-old wild-type Col-0 (left panel) and AIP10ko (right panel) plants. FIG. 4B shows a quantification of the average root length of AIP10ko and wild-type plants during development. FIG. 4C shows a quantification of the average number of lateral roots in AIP10ko and wild-type Col0-0 plants during development. The results show that root length is longer in AIP10ko plants all over development, and they develop more lateral roots.

FIGS. 5A-5C show images of shoot apex (FIGS. 5A and 5B) and rosette leaves (FIG. 5C) of AIP10 knockout (AIP10ko) and wild-type Col0-0 plants. FIG. 5A shows a microscopic image of the shoot apex of a representative wild-type Col0-0 plant 10 days after germination; and FIG. 5B shows a microscopic image of the shoot apex of a representative AIP10ko plant 10 days after germination. FIG. 5C shows images of the leaf series of one rosette of an 18-day-old representative wild-type Col0-0 plant (top panel) and an 18-day-old representative AIP10ko plant (bottom panel). The results show that the method of this disclosure generates plants with more organs, and in a higher speed, by demonstrating that AIP10 controls the timing of development of new organs.

FIG. 7A shows images of representative inflorescences of wild-type Col0-0 (left panel) and AIP10ko plants (right panel) 54 days after germination. FIG. 7B shows a graphical representation of average values of main axis height of a pool of 24 wild-type Col0-0 and 24 AIP10ko plants, 47 and 54 days after germination (DAG). FIG. 7C shows a graphical representation of the average values of the number of branches in the main axis of a pool of 24 wild-type Col0-0 and 24 AIP10ko plants, 47 and 54 days after germination (DAG). In FIGS. 7B and 7C, bars indicate average±standard deviation. A statistical analysis was performed by t-test (p-value <0.05). Asterisks (*) indicate significant changes between samples. The results show that the inflorescence main axis is longer and produces more branches in AIP10ko plants. Also, AIP10 silencing prolongs cell proliferation activity, delaying senescence that effectively lengthens the lifespan of the plant.

FIGS. 8A-8C show the increase in biomass and productivity in plants silenced for AIP10ko. FIG. 8A shows a graphical representation of the average values of fresh weight of rosette tissues of a pool of 15 wild-type and 15 AIP10 knockout (AIP10ko) plants, 20 and 27 days after germination (DAG). FIG. 8B shows a graphical representation of the average values of silique yield quantified in inflorescence main axis of 24 wild-type Col0-0 and AIP10 knockout (AIP10ko) plants, 47 and 54 days after germination (DAG). FIG. 8C shows a graphical representation of the average values of total seed yield per plant, in wild-type Col0-0 and AIP10 knockout (AIP10ko) plants. In FIGS. 8A, 8B and 8C, bars indicate average±standard deviation. A statistical analysis was performed by t-test (p-value <0.05). Asterisks (*) indicate significant changes between samples. The results demonstrate that the method of this disclosure leads to an increase in plant biomass and plant yield.

FIG. 9A shows a graphical representation of percentage of AIP10ko and wild-type Col0-0 plants that survived after 7 days without water irrigation (n=30), followed by normal irrigation. FIG. 9B shows a graphical representation of percentage of AIP10ko and wild-type Col0-0 plants that survived after 12 days without water irrigation (n=30), followed by seven days of normal irrigation. The results show that after a shorter period of 7 days without water, AIP10ko and wild-type Col0-0 plants had the same survival rate following irrigation; while after a prolonged period of 12 days without water, a higher percentage of AIP10ko survived. It demonstrates that the method of this disclosure produces plants more tolerant to drought stress.

FIG. 10A shows a graphical representation of the average values of the silique production per inflorescence main axis of wild-type Col-0 and AIP10 knockout (AIP10ko) plants that survived after a period of 7 days under water deficit, followed by normal irrigation. FIG. 10B shows a graphical representation of the average values of the silique production per inflorescence main axis of wild-type Col-0 and AIP10 knockout (AIP10ko) plants that survived after a period of 12 days under water deficit, followed by normal irrigation. In FIGS. 10A and 10B, bars indicate average ±standard deviation. A statistical analysis was performed by t-test (p-value <0.05). Asterisks (*) indicate significant changes between samples. The results show that AIP10ko plants maintain their higher yield compared to wild-type Col-0 plants after growing under drought stress, even after shorter periods of drought stress (7 days without irrigation), when the survival rates of AIP10ko and wild-type plants is similar. It demonstrates that the method of this disclosure produces plants with higher productivity when cultivated under drought stress.

FIG. 12A shows top views of the development of rosette from representative wild-type Col-0 plants (left panels) and representative RNAi-AIP10 plants (right panels) plants, 27 days after germination. FIG. 12B shows front views of the initial inflorescence development from wild-type plants Col-0 (left panel) and RNAi-AIP10 (right panel) plants, 27 days after germination. The results show that knockdown of AIP10 in RNAi-AIP10 plants increases the number and size of organs, leading to plants with increased final biomass, compared to wild-type plants, in a phenotype similar to that of AIP10 knockout plants. It demonstrates that different technologies to silence AIP10 gene expression in plants can be used for the method of this disclosure.

FIG. 13A shows front views of inflorescences from wild-type Col-0 plants (left panel) and RNAi-AIP10 plants (right panel), 31 days after germination (DAG). FIG. 13B shows front views of representative inflorescences from wild-type Col-0 plants (left panel) and RNAi-AIP10 plants (right panel), 54 days after germination (DAG). The results show that knockdown of AIP10 in RNAi-AIP10 plants increases the height and the number of inflorescences branches, compared to wild-type plants, in a phenotype similar to that of AIP10 knockout plants. It demonstrates that different technologies to silence AIP10 gene expression in plants can be used for the method of this disclosure.

DETAILED DESCRIPTION

Figure 1:
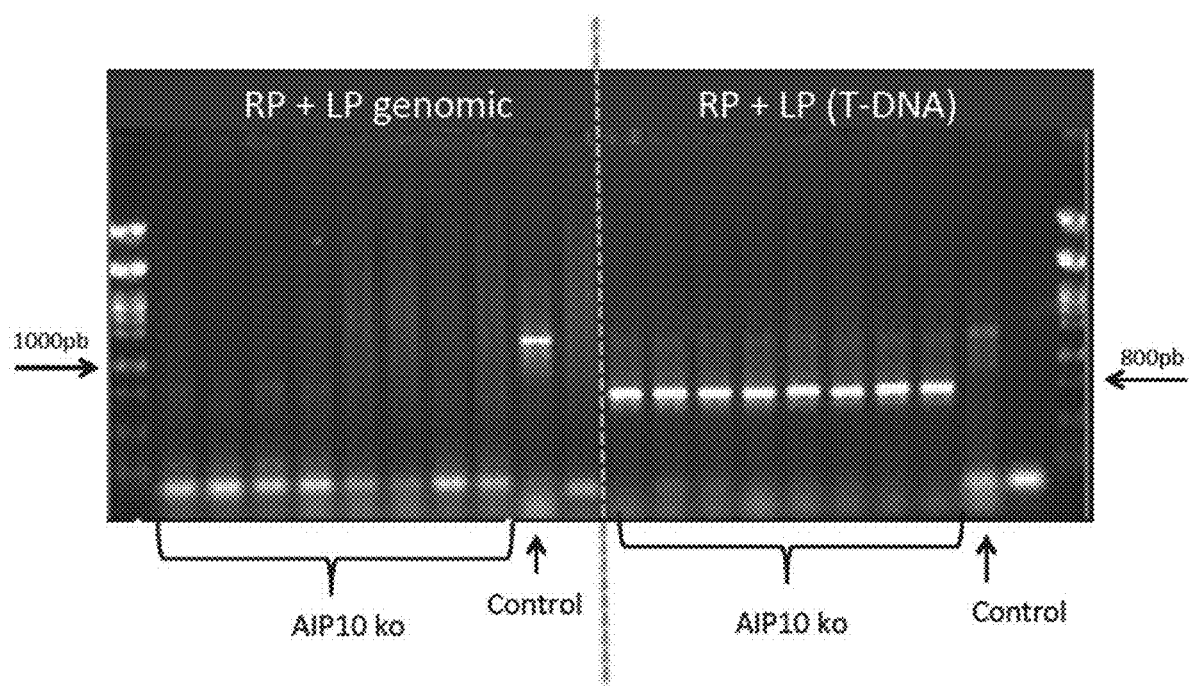
FIG. 1 shows a confirmation by PCR of the T-DNA insertion into the AIP10 gene from AIP10 knockout plants.

Described herein is the use of AIP1, or a variant thereof, to increase plant biomass and/or yield, and to increase drought tolerance. The use, as indicated here, is the use of the protein, and/or the use of a nucleic acid sequence (polynucleotide) encoding this protein, or the complement thereof The gene includes, but is not limited to, genomic DNA, cDNA, messenger RNA (including the 5' and 3' untranslated regions) and RNAi.

"Variants" as used herein, include, but are not limited to, homologues, orthologues and paralogues of SEQ ID NO:1 and SEQ ID NO:2 (AIP10 protein and its splicing variant, respectively). "Homologues" of a protein encompass peptides, oligopeptides, polypeptides, proteins and enzymes having amino acid substitutions, deletions and/or insertions relative to the unmodified protein in question and having similar biological and functional activity as the unmodified protein from which they are derived.

Paralogues are genes within the same species that have originated through duplication of an ancestral gene; orthologues are genes from different organisms that have originated through speciation, and are also derived from a common ancestral gene. Orthologues are genes from different organisms that have originated through speciation, and are also derived from a common ancestral gene.

Preferably, the homologue, orthologue or paralogue has a sequence identity at protein levels of at least 50%, 51%, 52%, 53%, 54% or 55%, 56%, 57%, 58%, 59%, preferably 60%, 61%, 62%, 63%, 64%, 65%, 66%, 67%, 68%, 69%, more preferably 70%, 71%, 72%, 73%, 74%, 75%, 76%, 77%, 78%, 79%, even more preferably 80%, 81%, 82%, 83%, 84%, 85%, 86%, 87%, 88%, 89% most preferably 90%, 91%, 92%, 93%, 94%, 95%, 96%, 97%, 98%, 99% or more when compared with SEQ ID NO:1 and SEQ ID NO:2, aligned or not, as measured using genomic analyses tools as, but not limited to, the programs BLASTp, Clustal and COBALT. As a non-limited example, orthologues of AIP10 (SEQ ID NO:1 and SEQ ID NO:2) are selected from the list consisting of SEQ ID NO:3-SEQ ID NO:23.

Increase of plant growth and/or yield is measured by comparing the test plant, comprising a gene used according to the method of this disclosure, with the parental, non-transformed plant, grown under the same conditions as control. Preferably, increase of growth is measured as an increase of biomass production. "Yield" refers to a situation where only part of the plant, preferably an economical important part of the plant, such as the leaves, roots or seeds, is increased in biomass.

The term "biomass" as used herein means an increase in weight/mass of certain parts of the plant, and can result from an increase in the area and/or increase in the quantity of this part of the plant.

The term "increase" as used herein means at least a 5%, 6%, 7%, 8%, 9% or 10%, preferably at least 15% or 20%, more preferably 25%, 30%, 35% or 40% more yield and/or growth in comparison to control plants as defined herein. Increase of plant growth, as used herein, is preferably measured as increase of any one or more of leaf biomass, root biomass and seed biomass.

Increase of plant drought tolerance is measured by comparing the test plant, comprising a gene used according to the method of this disclosure, with the parental, non-transformed plant, grown under the same conditions as control.

The term "increase in plant drought tolerance" as used herein means that test plants are able to support longer periods in soils with deficit in water availability, producing higher yields than the parental, non-transformed plant, grown under the same conditions. The term "increase" as used herein means at least a 5%, 6%, 7%, 8%, 9% or 10%, preferably at least 15% or 20%, more preferably 25%, 30%, 35%, 40%, 45% or 50% more yield and/or growth under drought conditions in comparison to control plants as defined herein.

In this disclosure, AIP10 expression is repressed or completely eliminated. Repression refers to the expression in the modified plant, compared with the non-modified parental plant, grown under the same conditions, and means a reduction or complete elimination of the mRNA levels and protein of the target gene or variants. Repression of gene expression can be realized, as a non-limiting example, by gene silencing, antisense RNA, RNAi, artificial microRNA, methodologies of genome editing (ZFN—"zinc-finger nucleases," TALENs—"transcription activator-like effector nuclease," CRISPR-Cas, and others), T-DNA insertion, transposons and others.

Design of RNAi and antisense RNA is known to the person skilled in the art. As a non-limiting example, RNAi can be designed with tools available on the internet. The RNAi can be directed against a part of the 5' untranslated terminal region, against a part of the coding sequence, and/or against the 3' terminal region of the mRNA. Some non-limiting examples of target sequences are: SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, and SEQ ID NO:19 of the Sequence Listing.

Also described herein are genetically modified plants, containing RNAi, or another method to decrease or eliminate gene expression, against a nucleic acid encoding AIP10 or a variant thereof, as defined above, to increase plant growth, biomass and tolerance against drought stress. This RNAi will target only a part of the nucleic acid, whereby the target sequence can be situated in the coding sequence, or in the 5' or 3' untranslated regions of the nucleic acid encoding AIP10 or variant.

A "genetically modified plant," as used herein, is a plant which genome was modified by a recombinant DNA construct and/or by genome editing, in which the referred recombinant DNA can be introduced directly by transformation or indirectly by inbreeding or crossings.

The RNAi against a nucleic acid encoding AIP10 or a variant thereof, or another method to decrease or eliminate gene expression, as defined above, means that the method is able to decrease or eliminate the expression of AIP10 or a variant in a non-modified parental plant.

Repression of expression of a target gene can be obtained by transfer of a genetic construct. The transfer of foreign genes into the genome of a plant is called transformation. Transformation of plant species is a fairly routine technique known to the person skilled in the art. Advantageously, any of several transformation methods may be used to introduce the gene of interest into a suitable ancestor cell.

The methods described for the transformation and regeneration of plants from plant tissues or plant cells may be utilized for transient or for stable transformation.

Transformation methods include, but are not limited to, Agrobacterium-mediated transformation, "floral dip," the use of liposomes, electroporation, chemicals that increase free DNA uptake, injection of the DNA directly into the plant, particle gun bombardment, transformation using viruses or pollen and microprojection.

Preferably, the plants used in the method of this disclosure are from the group of commercially cultivated plants and *Arabidopsis thaliana*. The term "commercially cultivated plants" as used herein means plants belonging to monocot, dicot and eudicot families, traditionally used in the agriculture, preferably, but not limited to: maize, soybean, cotton, sugarcane, sorghum, wheat, barley, millet, rye, oats, cocoa, beans, rice, grape, tomato, cassava, castor bean, papaya and poplar.

Described is a method of increasing plant biomass, plant yield and/or plant drought tolerance involves, but is not limited to: plant growth, RNA extraction, DNAse treatment, cDNA synthesis and cloning in plant expression vector, plant transformation and generation of genetically modified plants with the RNAi construct against AIP10 or variant, or another method to decrease or eliminate gene expression, as defined above.

Described herein are methods of utilizing (e.g., by down-regulating or reducing the expression of) the AIP10 gene (or a variant thereof) in a plant, so as to promote increased biomass, plant yield, and/or to promote plant drought tolerance. In such a use, the AIP10 may comprise a polynucleotide encoding a peptide of SEQ ID NO:1, SEQ ID NO:2, or a variant of either thereof. When a variant is used that is a homologue, or orthologue or paralogue variant of AIP10, it may have a sequence identity at the protein level of preferably at least 50%, 51%, 52%, 53%, 54%, 55%, 56%, 57%, 58%, 59%, 60%, 61%, 62%, 63%, 64%, 65%, 66%, 67%, 68%, 69%, more preferably 70%, 71%, 72%, 73%, 74%, 75%, 76%, 77%, 78%, 79%, even more preferably 80%, 81%, 82%, 83%, 84%, 85%, 86%, 87%, 88%, 89%, preferably more than 90%, 91%, 92%, 93%, 94%, 95%, 96%, 97%, 98%, 99% or more, when compared to SEQ ID NO:1, SEQ ID NO:2. Such use may take place in a plant species such as *Arabidopsis thaliana* or any other species such as those selected from the group consisting of monocot, dicot, and eudicot, particularly commercially cultivated plants, preferably, but not limited to: maize, soybean, cotton, sugarcane, sorghum, wheat, barley, millet, rye, oats, cocoa, beans, rice, grape, tomato, cassava, castor bean, papaya, poplar, and/or others.

In Vitro and In Vivo Plant Cultivation

To carry out the in vitro culture, *Arabidopsis thaliana* ecotype Columbia, plant knockouts for AIP10 obtained from the SALK bank of insertion mutants and RNAi-AIP10 plants were first grown in petri dishes with MS medium half strength. After 14 days growing in plates, the plants were transferred to pots containing autoclaved soil and vermiculite (3:1).

For sterilization, seeds of *A. thaliana*, kept at 4° C., were placed in microcentrifuge tubes containing 1 ml of 70% ethanol for two minutes. After removal of the ethanol, the seeds were placed in a sodium hypochlorite solution with 5% TWEEN® and 0.025% for 10 minutes. The samples were washed five times with autoclaved distilled water.

The sterilized seeds were placed on plates with solid culture medium with the aid of autoclaved sticks. The plants were grown in a greenhouse at 21° C. with a photoperiod of 10 hours of light and 14 hours of darkness.

To carry out the in vivo cultivation of *A. thaliana*, the plants were transferred to pots containing autoclaved vermiculite and soil (3:1) after 14 days of in vitro growing on plates. The plants were grown in a greenhouse at 21° C. with a photoperiod of 16 hours of light and 8 hours of darkness. The plants were collected for molecular and phenotypic analysis, at varying times after cultivation and in some cases after different regimes of suspension and resumption of water irrigation.

RNA Extraction

The collected plant material was immediately frozen in liquid nitrogen and stored in a freezer at −80° C. For RNA extraction, the material was macerated in liquid nitrogen and rapidly transferred to 1.5 ml microtubes containing 500 uL of TLE buffer (200 mM Tris-Cl, 100 mM LiCl, 5 mM EDTA, 1% SDS, pH 7.5) 250 µL 250 µL of phenol and chloroform. The microtubes were stirred for 1 minute and centrifuged at 12000 g for 20 minutes at 4° C. After centrifugation, the aqueous phase was transferred to microcentrifuge tubes and was added to one volume of chloroform: isoamyl alcohol (24:1). The new mixture was stirred for 1 minute and centrifuged at 20000 g for 15 minutes at 4° C. The aqueous phase was transferred to microcentrifuge tubes and 1 volume of 6 M LiCl with diethyl pyro-carbonate (DEPC) 0.1% was added. The tube was shaken for 1 minute and kept at 4° C. for 16 hours. The next day, tubes were centrifuged at 12000 g for 20 minutes at 4° C., the supernatant discarded and the precipitate solubilized in 1 ml 3M LiCl, DEPC 0.1%. The tubes were again centrifuged at 12000 g for 20 minutes at 4° C., the supernatant discarded and the precipitate solubilized in 250 µl $H_2O$ with 0.1% DEPC. 1/10 volume of 3 M NaOAc pH 4.8 with 0.1% DEPC and 2 volumes (considering the amount of added NaOAc) of absolute ethanol were added to these samples. The samples were homogenized and incubated for 30 minutes at −80° C. or for 2 hours at −20° C. After incubation, the tubes were again centrifuged at 12000 g for 20 minutes at 4° C., the supernatant was discarded and the precipitate was washed with 1 mL of 70% ethanol with 0.1% DEPC. Again, the tubes were centrifuged at 12000 g for 20 minutes at 4° C., the supernatant was discarded and the precipitated RNA was solubilized in 20 µl $H_2O$ with 0.1% DEPC.

DNAase Treatment

Total RNAs were treated with DNase I (New England Biolabs) to eliminate any contamination with genomic DNA. 0.5 U of DNAse I was used for each 1 µg of total RNA in enzyme buffer (200 mM Tris-Cl pH 8.3, 500 mM KCl, 25 mM MgCl2, 0.1% DEPC). RNAs were incubated with buffer and DNAse at 37° C. for 15 minutes. The RNA was purified by adding 1 volume of phenol, the phases were mixed by vortexing and then centrifuged at 20000 g for 10 minutes. The aqueous phase was transferred to a fresh tube to which was added 1 V of chloroform. A new centrifugation at 20000 g for 10 minutes was carried out and the aqueous phase was transferred to a new tube. The RNA was then precipitated by adding 1/10 V 3 M NaOAc 0.1% DEPC and 2 V of absolute ethanol, followed by incubation at −80° C. for 20 minutes, and centrifuged at 20000 g for 20 minutes. The supernatant was discarded and the precipitated RNA was washed with a solution of 70% ethanol with 0.1% DEPC, after which it was solubilized in MILLI-Q® water with 0.1% DEPC.

cDNA Synthesis

After treatment with DNAse, the first strand cDNA was synthesized using the SUPERSCRIPT® III reverse transcriptase with total RNA samples (Invitrogen). The following protocol enables cDNA synthesis in a reaction where there is a range of 10 ng to 5 µg of total RNA. It was added into a microtube of 0.5 ml: 1 µL oligonucleotide Oligo (dT)20 (50 mM); 10 ng-5 µg of total RNA; 1 µL dNTP (10 mM) and the volume was complete with sterile distilled $H_2O$ to 13 µL. The mixture was heated at 65° C. for 5 minutes and incubated on ice for 1 minute. After, 4 µL of 5× First-Strand Buffer (Buffer first tape); 1 µL DTT (0.1 M); 1 µL of RNAseOUT Recombinant RNase Inhibitor (40 U/µL) and 1 µL of SUPERSCRIPT® III (200 U/µL) were added to the microtube. The reaction was incubated at 50° C. for 60 minutes and then inactivated at 70° C. for 15 minutes. To remove remaining RNA, 2 U of RNaseH (USB, Affymetrix) were added to the microtube, and it was incubated at 37° C. for 15 minutes.

Amplification Reactions—PCR

The AIP10 amplification PCR reactions were performed in a MJ-Research thermocycler (PTC-100) using the following conditions:

94° C. for 5 minutes
94° C. for 1 minute
55° C. for 1 minute
72° C. for 30 seconds
72° C. for 5 minutes
Steps 2, 3 and 4 were repeated for 35 cycles.

The following primers were used for amplification:

```
AttB1:
                                         (SEQ ID NO: 24)
AAAAAGCAGGCTTCACAATGGAGAAAGGGGTTGGA

AttB2:
                                         (SEQ ID NO: 25)
AGAAAGCTGGGTTTGATGAGAACTAGCTTAGGGTTC
```

After PCR amplification, the generated fragments were verified on a 1% agarose gel. The bands with DNA fragments with the size of interest were excised from the gel and placed in a microcentrifuge tube. The kit Wizard SV Gel and PCR Clean-Up System (Promega) was used to make the purification of genes. After elution, the DNA was quantified using a NANODROP®2000 Spectrophotometer (Thermo Scientific).

Entry Clone Construction

After purification of the fragments of interest from the agarose gel, a reaction between the recombination sites attB1 and attB2 placed in the fragment using the primers and AttP1 and AttP2 sites present in the vector pDONR221 (Invitrogen) was performed. This reaction, called BP is part of the Invitrogen Gateway technology, and utilizes the gateway kit BP clonase II Enzyme mix. To the reaction, 1 to 7 µL of the purified PCR product from the 1% agarose gel to a final amount of 15 to 150 ng; 1 µL of pDONR221 (150 ng/µL); 2 µL BP clonase II enzyme mix; and autoclaved MILLI-Q® water to a final volume of 10 µL were pipetted in a microtube of 1.5 mL. The reactions were incubated at 25° C. for 1 hour and at the end of this time, the reaction was stopped by adding 1 µL of proteinase K and incubating at 37° C. for 10 minutes. After completion of the BP reaction, the samples were dialyzed for 3 hours in 0.025 µm membranes (Millipore).

Electroporation

For electroporation, 40 µl of electro-competent bacteria were used. The electroporation was done in an electroporation cuvette of 1.8 KV to 25 µF and 200Ω in an Eppendorf eletroporador as described by Ausubel et al. (1992).

AIP10 Cloning in Expression Vectors

After the formation of the entry clone, the transfer of AIP10 gateway to another vector was made through a recombination reaction called LR. In this reaction, the gene of interest is transferred to other plasmids with ATTR recombination arms. This reaction also is part of the Invitrogen Gateway technology, and utilizes the Gateway LR clonase II kit Enzyme mix. To the reaction, it was pipetted: 75 ng the destination vector, 150 ng entry clone, 1 μL LR buffer, 0.5 μL of enzyme LR and autoclaved MILLI-Q® water to a final volume of 5 μL. The reactions were incubated at 25° C. for 1 hour. The recombination reaction was dialyzed for three hours in a 0.025 μm membrane (Millipore).

A. thaliana Transformation

Agrobacterium tumefaciens containing the plasmid of interest was inoculated into LB medium without antibiotics and incubated at 28° C. under shaking conditions for eight hours. After this time, 9 ml of LB without antibiotic was added to the culture of these bacteria and were incubated at 28° C. under agitation until the OD 2.0 at 600 nm. 40 ml of MILLI-Q® water containing 10% sucrose and 0.05% SIL-WET® were added to the A. tumefaciens culture and this mixture was used immediately.

A. thaliana plants growing in soil with inflorescence stems of 7 to 10 cm were immersed in the mixture containing the bacteria for 2 to 3 seconds according to the established protocol (CLOUGH; BENT, 1998). These plants were covered with plastic PVC and kept in a humid environment at 21° C. for 24 hours. After this time, the plastic was removed and the plants were kept in a greenhouse at standard growth conditions.

Selection of Mutants

The strains of transformed plants (T0) had their seeds collected, and they were plated on selective medium (vectors used in the selection was 50 μg/mL kanamycin). The resistant plants (T1) were transferred to the soil and the seeds were collected. T1 seeds generated T2 plants that were analyzed for segregation.

cDNA Synthesis for RT-PCR Analysis in Real Time

The first strand cDNA was synthesized using the kit "TAQMAN® First strand cDNA synthesis" and it was performed in reactions with a final volume of 25 μL, according to the manufacturer. For each reaction, 500 ng of total RNA were added plus 2.5 μl 10× TAQMAN® RT buffer, 25 mM of MgCl2 5.5 μl dNTPs Mix, 1.25 μl of random hexamer, 0.5 μl RNase inhibitor, 0.625 μl of MULTISCRIBE™ Reverse Transcriptase (50 U/μl). The samples were incubated at 25° C. for 10 minutes, followed by 48° C. for 30 minutes and a final step at 95° C. for 5 minutes. Samples were diluted four times with 10 mM Tris-Cl pH 8.0 and stored at −20° C. or used immediately.

Real-time PCR

The real-time PCR was performed with SYBR Green PCR Master Mix kit of the company Applied Biosystems, according to manufacturer's recommendations. The reaction was performed in a 96-well plate (MicroAmp Optical 96-Well Reaction Plate, Applied Biosystems Company). In each well, 1 μl of the first strand reaction was placed, 5 μl of the kit mix solution, and 4 μl of a mixture of the two oligonucleotides at 10 mM each. For each reaction, which used the specific oligonucleotides for each gene, another reaction with primers specific for the ubiquitin 14 gene (UBI14) was taken as a constitutive gene in all plant cells. This reaction was used as a positive control and to normalize the amount of first strand cDNA used in the experiments. As a negative control, a reaction was made in the same positive control conditions without the first strand cDNA.

To normalize the samples by the amount of first strand cDNA used, the fluorescence value of each sample with primers specific for the gene in question was then divided by the fluorescence value of the sample with the UBI14 primer.

Fl. Rel.=2 (CT Ubi-CT gene)
Where,
Fl. Rel. Is the relative fluorescence.
Ubi CT is the average number of cycles in the chosen point of the control with Ubi14.
CT gene is the average number of cycles in the chosen point of the gene in question.

To calculate the relative expression of the experiments with the experimental control, the following relationship was made: Fl.Rel.Exp/Fl.Rel cont.

The primers used in real-time PCR experiments are below:

Primer Sequence

```
AIP10 forward:
                              (SEQ ID NO: 26)
GGAGCTGAAGAACCCTAAGCTAGTT AIP10 reverse:
                              (SEQ ID NO: 27)
GGACGAGACAAATCTACAAAAGAATAAA UBI-14 forward:
                              (SEQ ID NO: 28)
TCACTGGAAAGACCATTACTCTTGAA UBI-14 reverse:
                              (SEQ ID NO: 29)
AGCTGTTTTCCAGCGAAGATG
```

Biomass of Vegetative Part

To verify the biomass of A. thaliana rosettes, AIP10 knockout plants and RNAi-AIP10, and control plants, of 27 days were collected and immediately weighed on a precision balance. Data were statistically analyzed and considered different (t-test).

Biomass and Productivity of the Reproductive Part

Measurements of height, silique production and seed yield were made with AIP10 knockout plants and RNAi-AIP10, and compared with control plants.

The height of the main axis of the plants was measured with the aid of a measuring tape and the number of siliques produced was counted throughout the development. Data were statistically analyzed and considered different (t-test).

The production of seeds of each plant was individually evaluated. Seeds were collected, and the total number of seeds produced by each individual was weighed on a precision scale and the values obtained were analyzed and considered statistically different (t-test).

Tolerance to Drought Stress

To evaluate the tolerance to water stress, plants were cultivated and watered normally for 25 days. Then watering was suspended for 7 days in a group of plants, and for 12 days in the other group. After this period, watering was resumed and after 7 days, plant survival rate was evaluated. At the end of development, the number of siliques produced by each individual was counted. Data were statistically analyzed and considered different (t-test).

Results

Increase in Biomass and Yield in AIP10 Knockout Plants.

Figure 2:
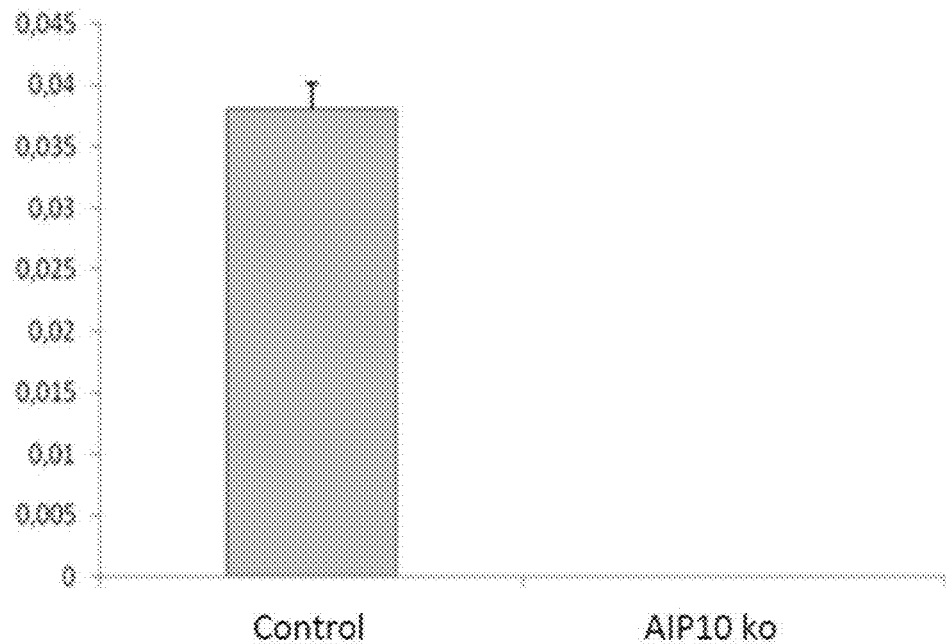
FIG. 2 shows a graphical representation of the average values of AIP10 mRNA levels in whole AIP10 knockout (AIP10ko) seedlings, 8 days after germination, analyzed by qRT-PCR and normalized by UBI14 mRNA levels. Data shown represent average values obtained from independent amplification reactions (n=3) and biological replicates (n=2). Each biological replicate was performed with material collected from a pool of at least six plants. Bars indicate average±standard deviation of biological replicates.

In order to better understand the function of the AIP10 gene, knockout plants for the gene were obtained in the SALK collection of insertion mutants. Confirmation of the T-DNA insertion was identified by PCR (FIG. 1) and confirmation of absence of AIP10 mRNA was made by qRT-PCR (FIG. 2). To evaluate the effect of silencing the expression of AIP10 on the development of A. thaliana, knockout and wild plants were grown under the conditions described above. FIGS. 3A-3E show the phenotypical differences in plants with reduced levels of AIP10. These plants have larger rosette leaves and more developed roots.

Figure 4A:
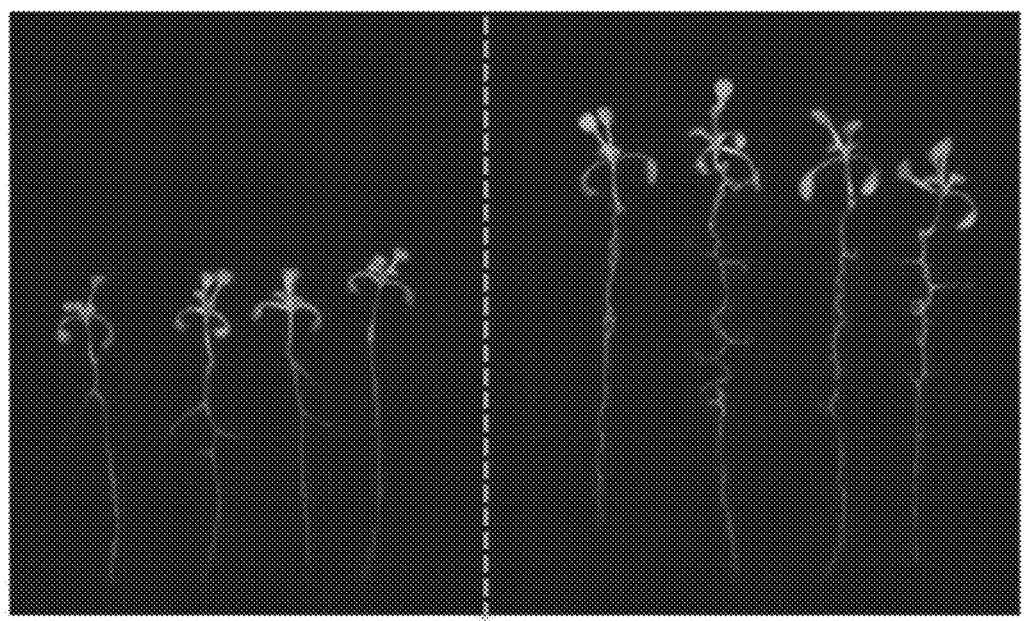
FIGS. 4A-4C show the root development of AIP10 knockout (AIP10ko) and wild-type Col0-0 plants.
Figure 4B:
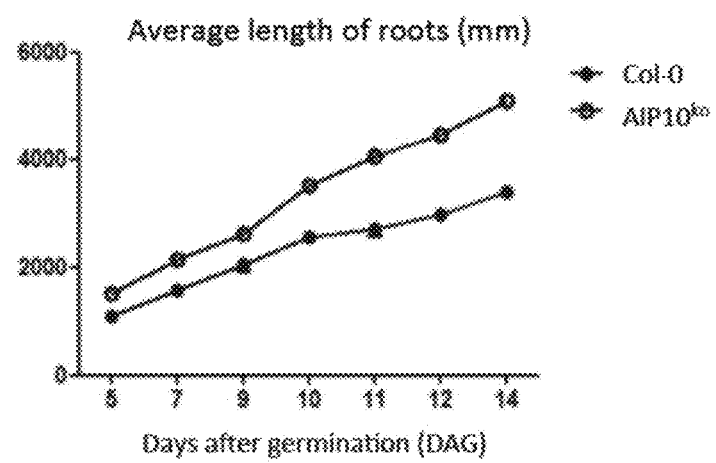
Figure 4C:
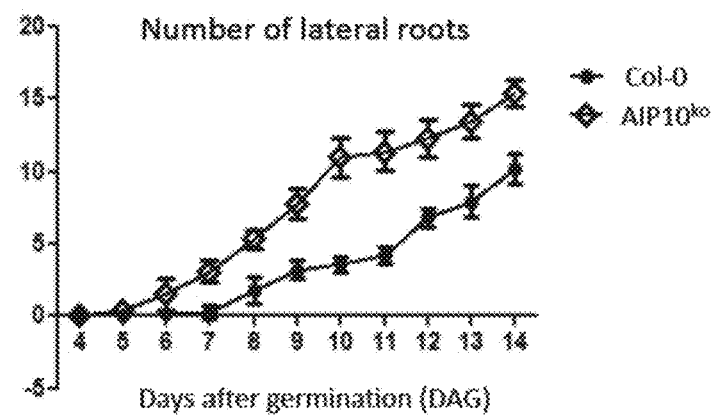
Figure 5C:
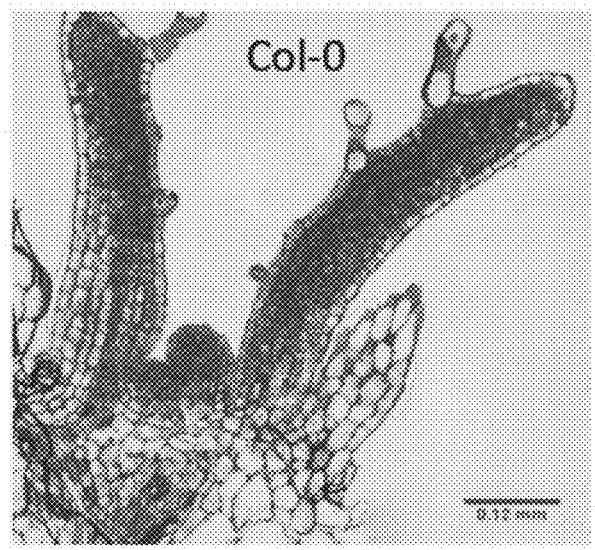
Figure 5C:
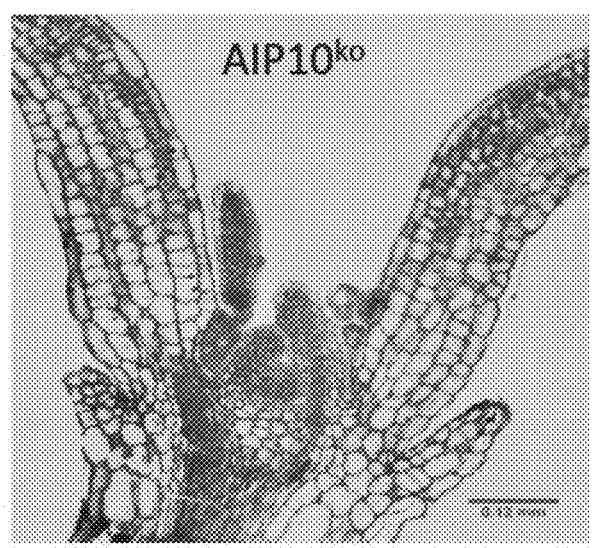
Figure 5C:
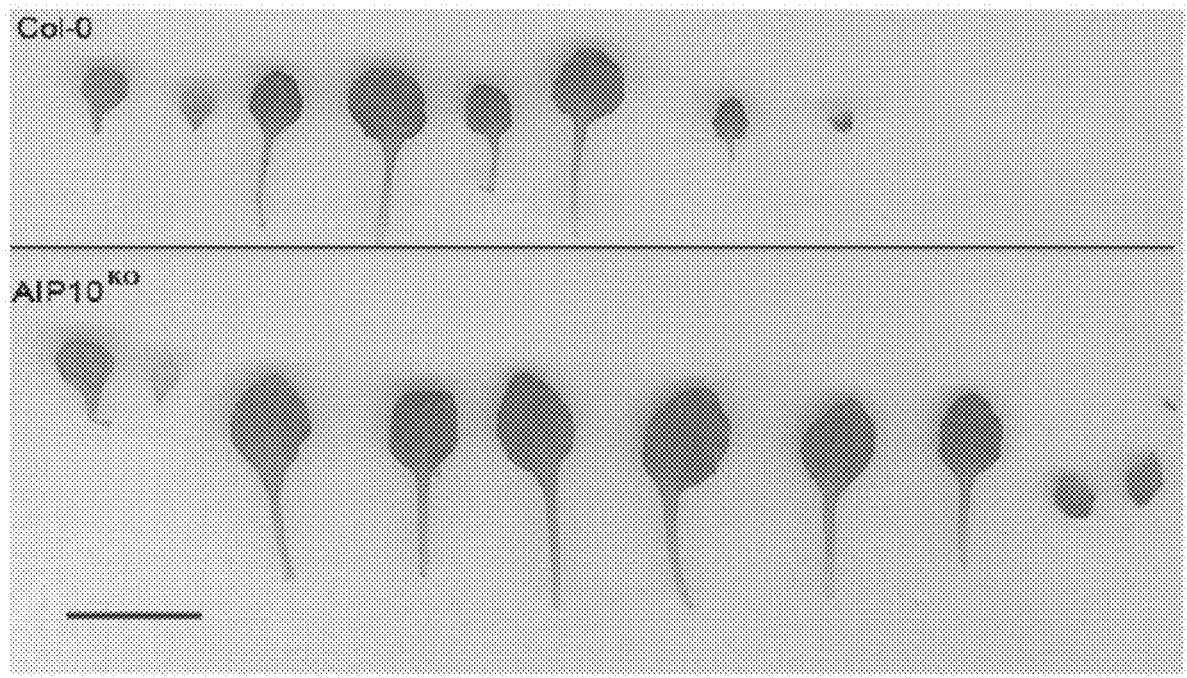
Figure 6A:
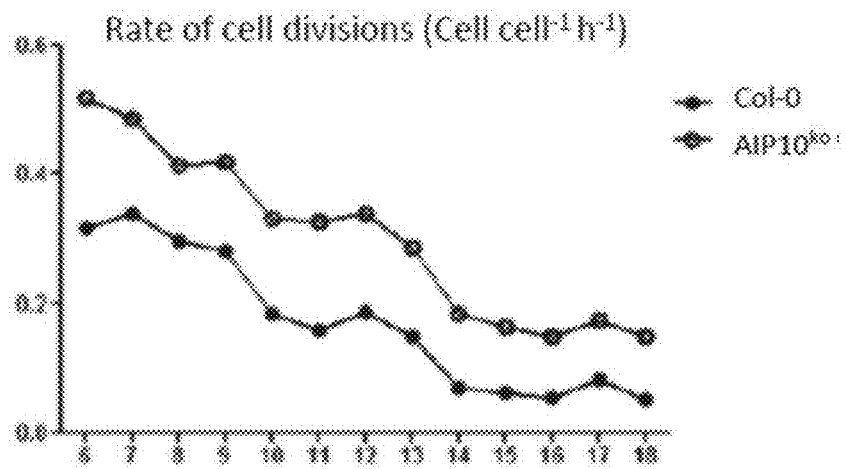
FIGS. 6A-6C show the calculation of cell division rates (FIG. 6A), cell numbers (FIG. 6B) and leaf area (FIG. 6C) by kinematic studies of developing leaves from AIP10 knockout (AIP10ko) and wild-type Col-0 plants. The results show that AIP1Oko leaves have higher rates of cell division during a prolonged period, higher number of cells and larger area of leaves. It demonstrates that the method of this disclosure controls the growth and final size of organs in plants by regulating cell division rates and final cell numbers.
Figure 6B:
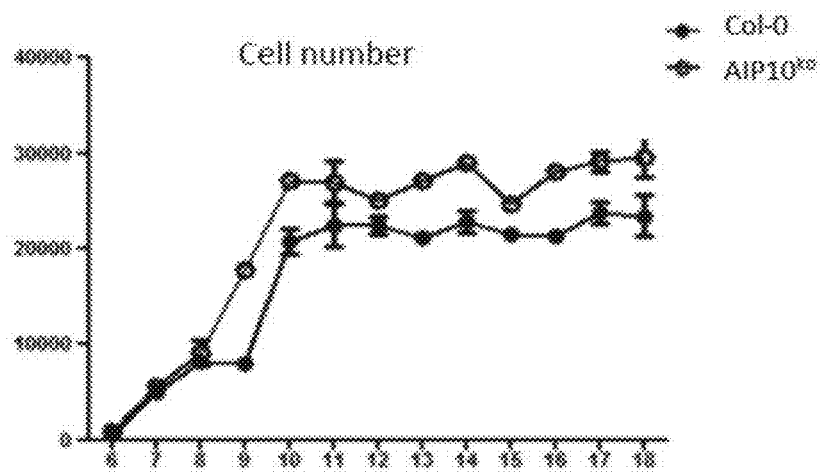
Figure 6C:
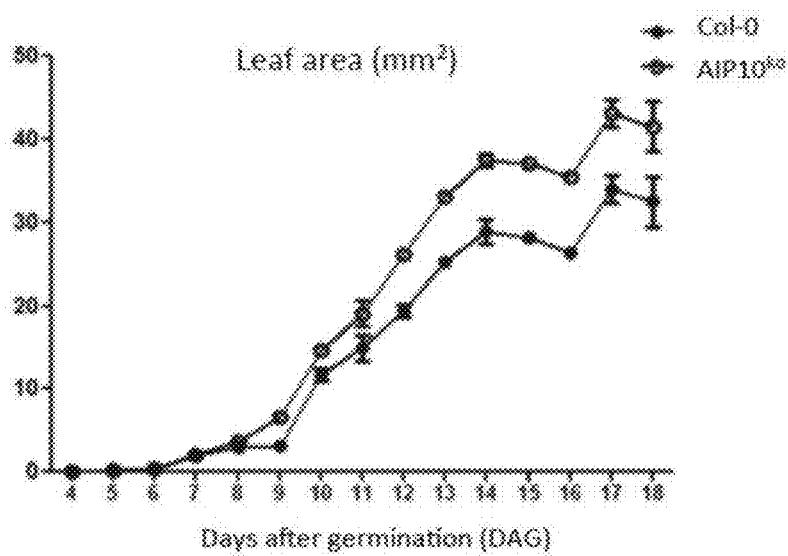
Figure 7A:
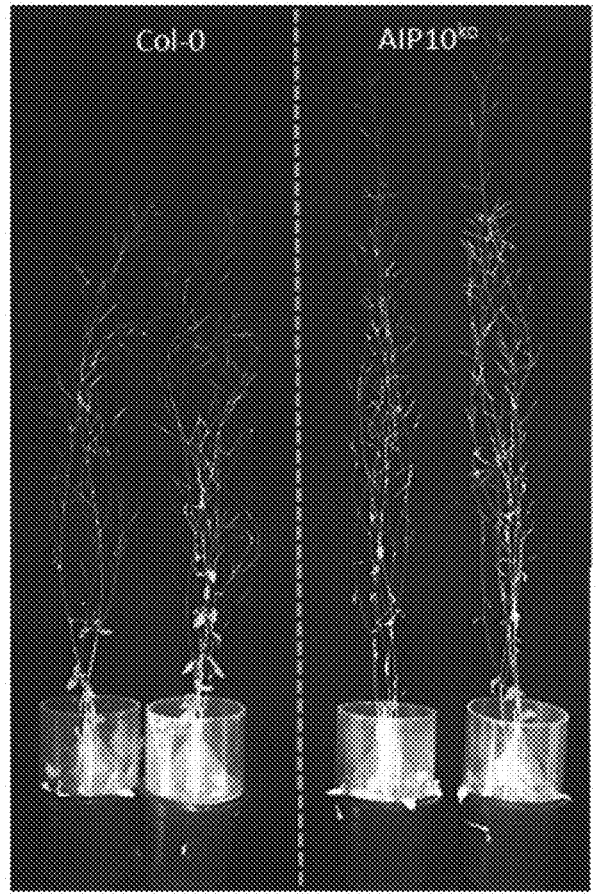
FIG. 7A-7C show development of the reproductive phase in AIP10 knockout (AIP10ko) and wild-type Col0-0 plants.
Figure 7B:
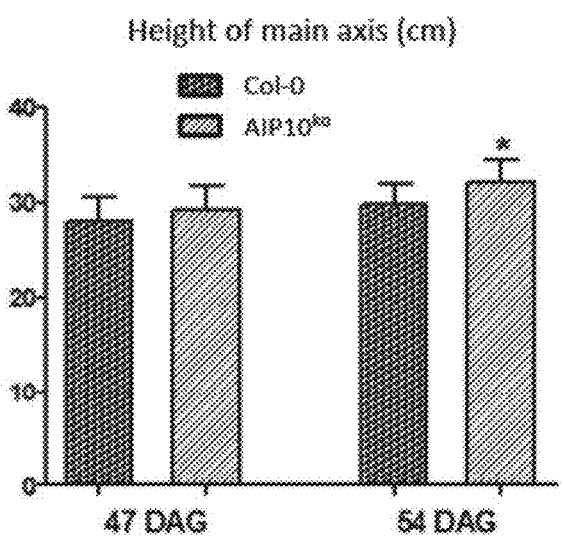
Figure 7C:
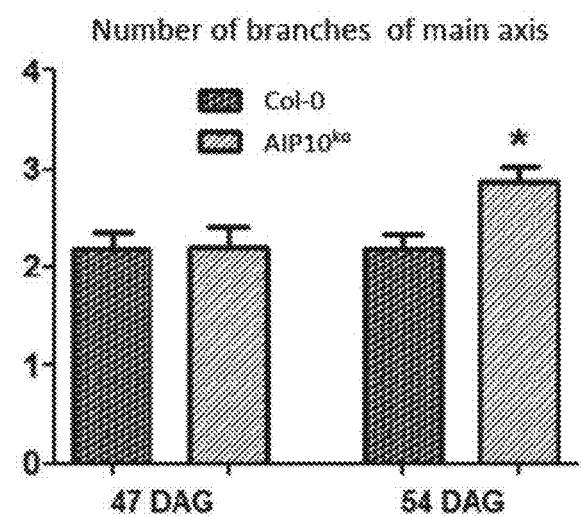

To understand which developmental processes AIP10 is controlling in plants, phenotype of plants silenced for AIP10 (AIP10ko) was characterized along development. The analyses showed that root length is longer in AIP10ko plants all over development (FIGS. 4A, 4B), and they develop more lateral roots (FIGS. 4A, 4C) compared to wild-type plants. In the aerial part, AIP10ko plants develop more leaves, and in a higher speed (FIGS. 5A-5C), demonstrating that AIP10 controls the timing of development of new organs. Kinematics studies of leaf development showed that AIP10ko leaves have higher rates of cell divisions during a prolonged period (FIG. 6A), higher number of cells (FIG. 6B) and larger area of leaves (FIG. 6C). It shows that AIP10 controls the growth and final size of organs in plants, by regulating cell division rates and final cell numbers. During the reproductive phase, AIP10ko plants produce inflorescence main axis longer and with more branches, compared with wild-type plants (FIGS. 7A-7C). All together, the data shows that silencing of AIP10 increases cell division rates in all main plant indeterminate meristems (root apical meristem, root pericycle, shoot apical meristem and inflorescence), leading to meristems formed with more cells. By speeding cell divisions and the provision of differentiating cells, AIP10ko organogenesis might be accelerated, developing plants with increased cell number and biomass. Also, AIP10 silencing prolongs cell proliferation activity, delaying senescence, which effectively increases organs sizes and lengthens the lifespan of the plant.

To quantify AIP10ko biomass, within 27 days after germination, rosettes of control and mutant plants were collected for measuring the fresh weight (FIG. 8A). Knockout plants have greater fresh weight than control plants. The production of siliques and seeds in control and AIP10 knockout plants was also quantified. Silique yield quantified in inflorescence main axis was higher in AIP10ko plants, compared with wild-type plants (FIG. 8B). The amount of seed produced by each plant was weighed separately (FIG. 8C) in order to quantify the yield of plants. Plants knockout to AIP10 produced about 30% more seeds than control plants. These results demonstrate that the method of this disclosure leads to an increase in plant biomass and an increase in fruit and seed yield.

Increase in Drought Tolerance in AIP10 Knockout Plants.

Figure 9A:
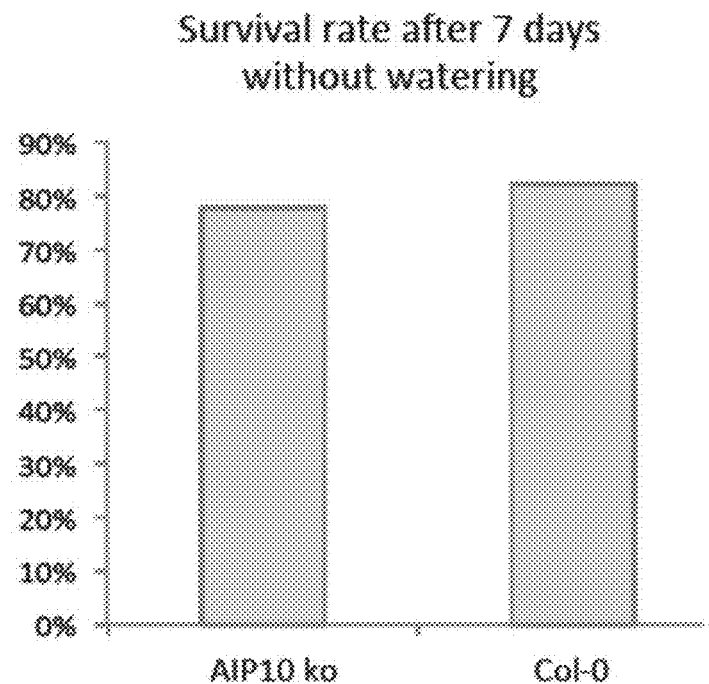
FIGS. 9A and 9B show the survival rates of AIP10 knockout (AIP10ko) and wild-type Col0-0 plants after water deficit conditions.
Figure 9B:
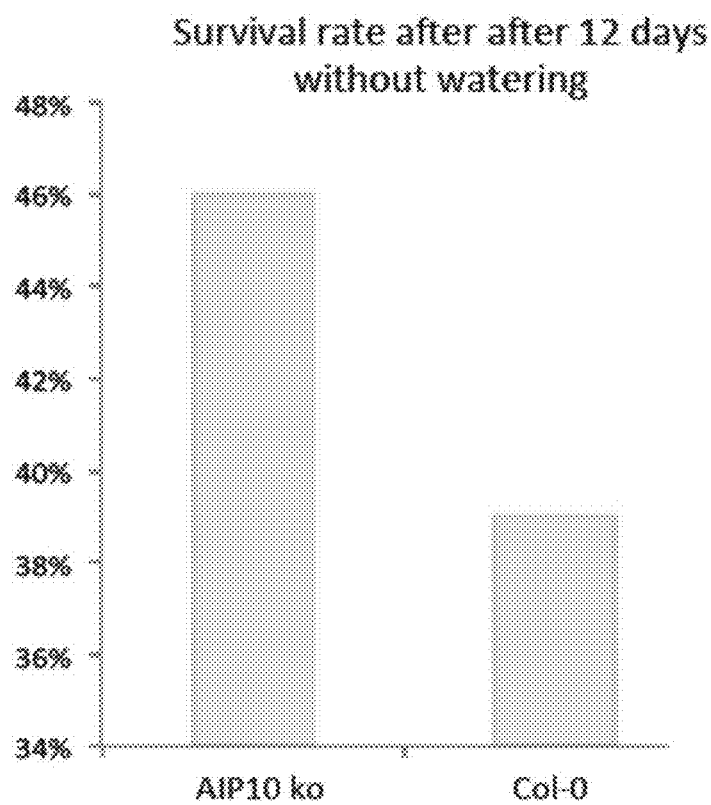

Wild-type and AIP10 knockout plants were cultivated and watered normally until they are 25 days old. After this period, a group was subjected to water stress for 7 days and another for 12 days. After these periods, the plants returned to be watered noilnally. The survival rates of AIP10 knockout and wild-type plants were measured after water deficit conditions (FIGS. 9A and B). After a shorter period (7 days) without water, AIP10ko and wild-type Col0-0 plants had the same survival rates following irrigation; while after a prolonged period of 12 days without water, a higher percentage of AIP10ko plants survived. It demonstrated that the method of this disclosure produces plants more tolerant to drought stress.

Figure 10A:
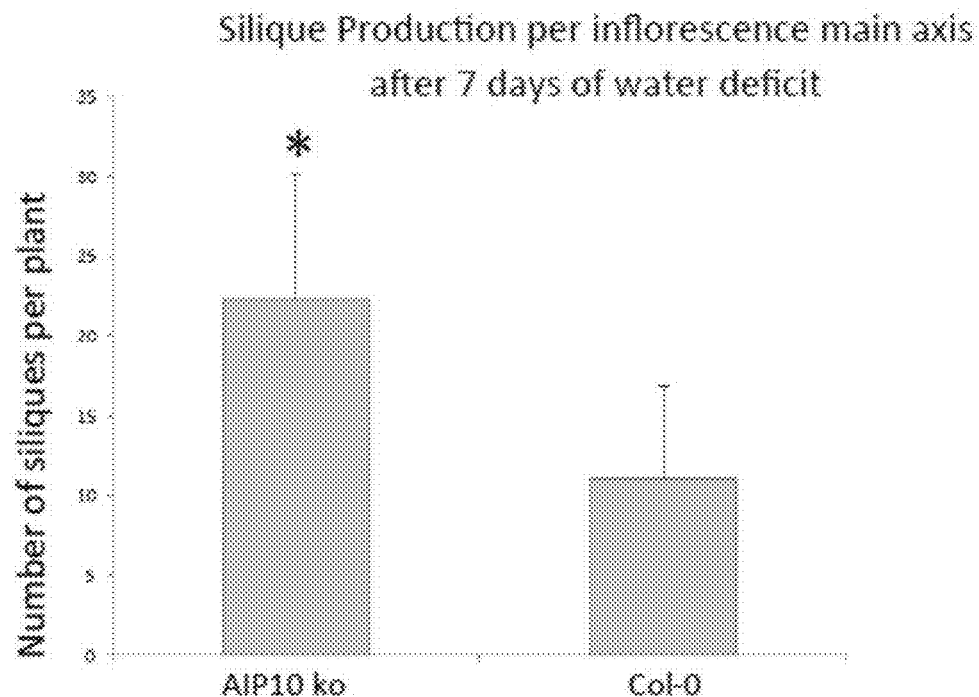
FIGS. 10A and 10B show the productivity of wild-type Col-0 and AIP10 knockout (AIP10ko) plants that survived after a period of water deficit.
Figure 10B:
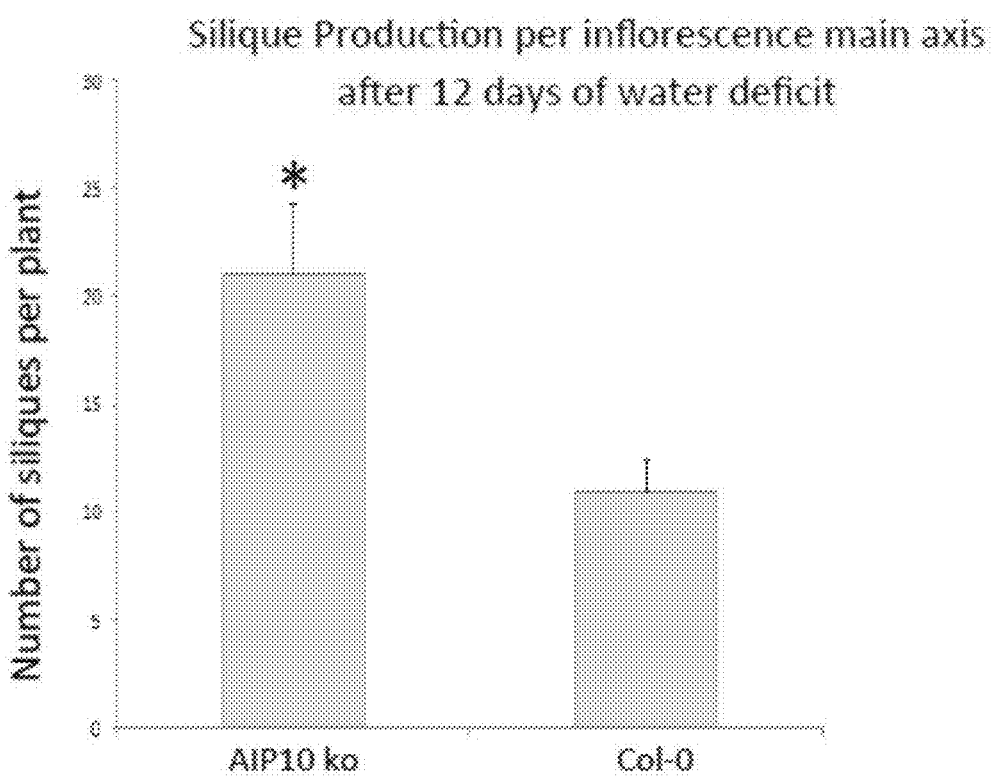

To assess the productivity of these plants after the water stress, the number of siliques produced by plants that survived the stress was evaluated (FIGS. 10A and 10B). AIP10ko plants produced more siliques than wild-type plants after growing under drought stress, even after shorter periods of drought stress (7 days without irrigation), when the survival rates of AIP10ko and wild-type plants was similar. It demonstrated that the method of this disclosure produces plants with higher productivity when cultivated under drought stress.

Increase in Biomass and Yield in Plants with Reduced Levels of AIP10 (AIP10 RNAi Construct)

Figure 11:
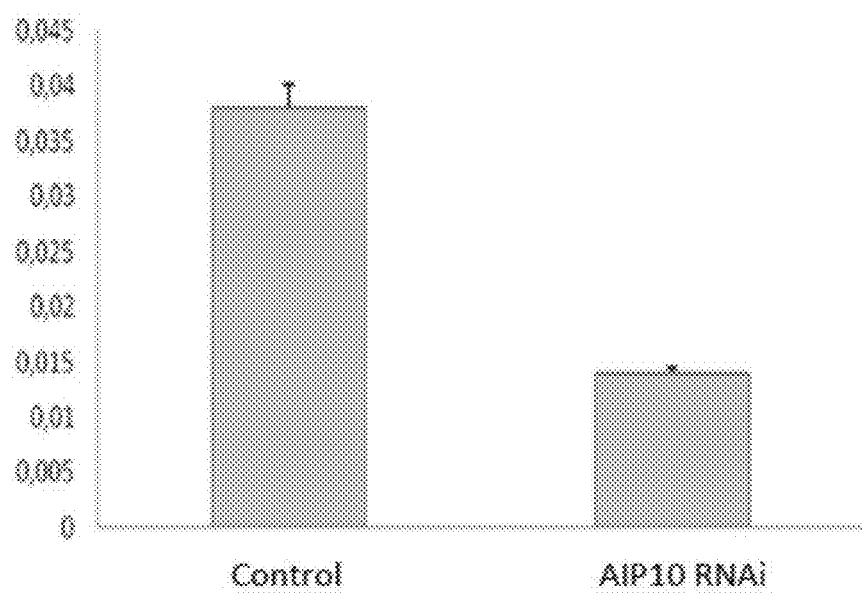
FIG. 11 shows a graphical representation of the average values of AIP10 relative expression in leaves of RNAi-AIP10 and wild-type plants 25 days after germination, analyzed by qRT-PCR and normalized by UBI14 mRNA levels. Data shown represent average values obtained from independent amplification reactions. Each biological replicate was performed with material collected from a pool of at least six plants. Bars indicate average ±standard deviation of biological replicates.

To evaluate the effect of AIP10 RNAi construct on the development of *A. thaliana*, wild-type plants transformed with the construct were grown under the conditions described above and their phenotype was evaluated. It was confirmed by qRT-PCR that plants transformed with the construct have reduced levels of AIP10 (FIG. 11).

Figure 12A:
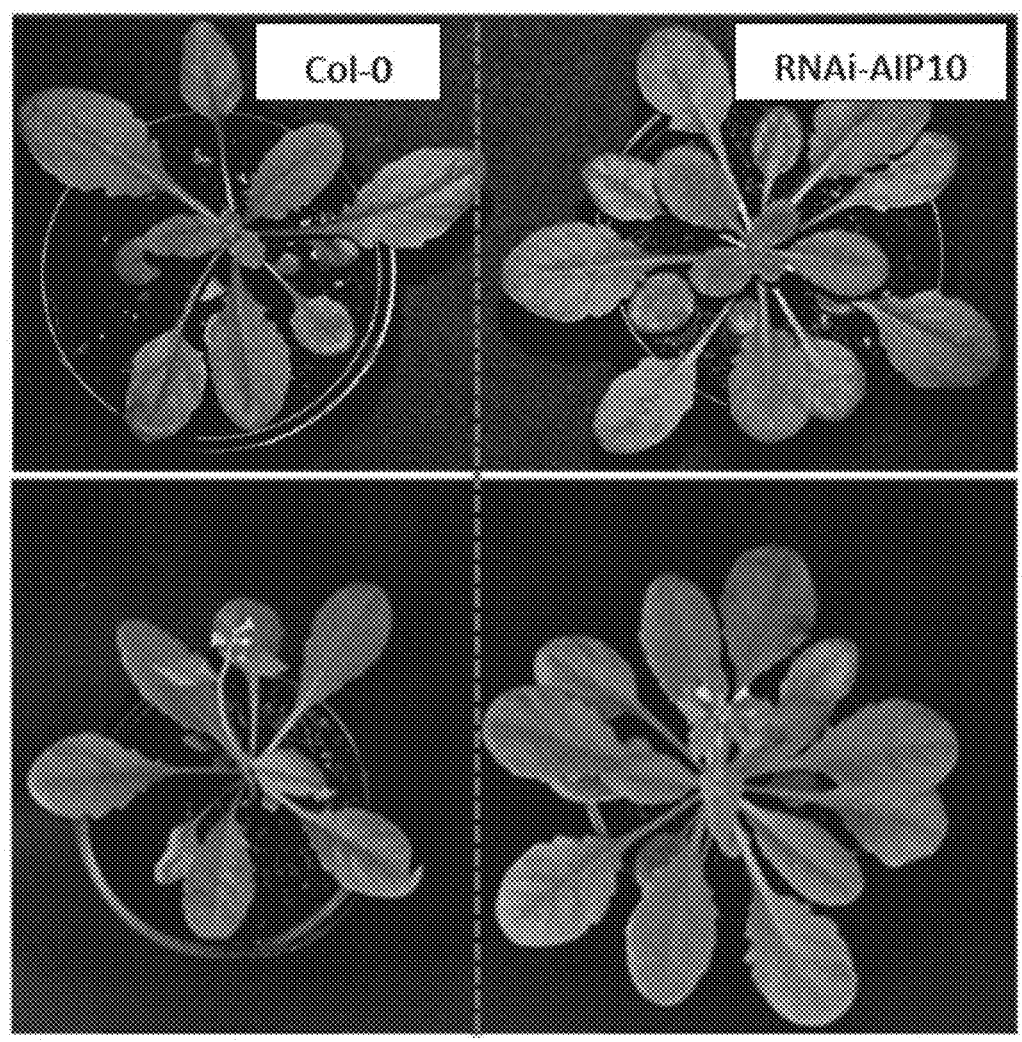
FIGS. 12A and 12B show images of RNAi-AIP10 and wild plants Col-0 plants.
Figure 12B:
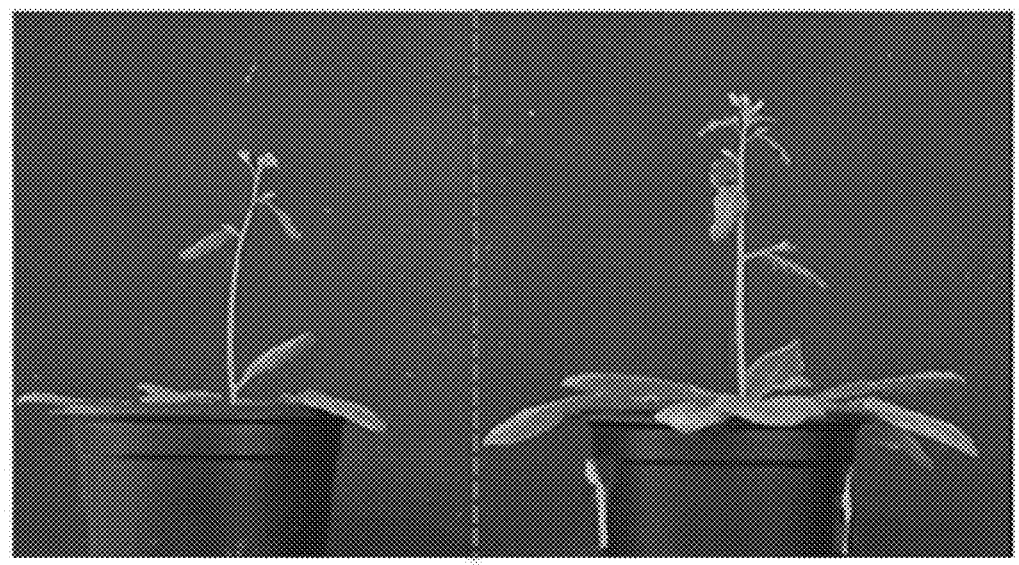
Figure 13A:
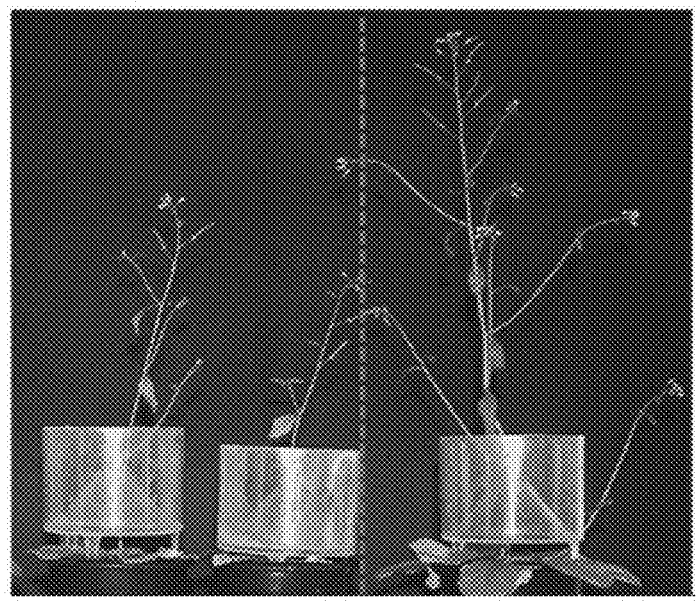
FIGS. 13A and 13B show development of the reproductive phase in RNAi-AIP10 and wild-type Col-0 plants.
Figure 13B:

As can be seen in FIG. 12, plants with reduced levels of AIP10 (containing the RNAi construct) have more leaves than control plants, as well as larger leaves, showing increased final biomass, in a phenotype similar to that of AIP10 knockout plants. In FIG. 13, it can be seen that inflorescence of plants with reduced levels of AIP10 are taller and have more branches, in a phenotype similar to that of AIP10 knockout plants.

The results show that the reduction in AIP10 levels is responsible for increasing plant biomass and/or yield and/or drought tolerance. The data also show that different technologies can be used as a method for reducing or eliminating AIP10 levels. Among them, the insertion of T-DNA, transposons, artificial microRNA, RNAi, antisense RNA, methodologies of genome editing, among others, can be used.

Although particular embodiments of the method of this disclosure have been shown and described, various combinations, changes and modifications may be made in this disclosure to meet specific needs without departing from the disclosure and from its broader aspects. In addition, while a particular feature of the disclosure may have been disclosed with respect to only one of several embodiments, such feature may be combined with one or more other features of other embodiments, as far as may be desired and advantageous for any particular application.

REFERENCES (the contents of each of which are incorporated herein by this reference):

Aladjem M. I. Replication in context: dynamic regulation of DNA replication patterns in metazoans. *Nature Reviews Genetics*, v. 8, n. 8, pp. 588-600, 2007.

Berckmans B. and L. De Veylder. Transcriptional control of the cell cycle. *Current opinion in plant biology*, v. 12, n. 5, pp. 599-605, 2009.

Blow J. . and A. Dutta. Preventing re-replication of chromosomal DNA. *Nat. Rev. Mol. Cell. Biol.*, v.6, n.6, pp. 476-86, 2005.

FAO-FOOD AND AGRICULTURE ORGANIZATION OF THE UNITED NATIONS. The State of Food Insecurity in the World Economic crises—impacts and lessons learned. [s.l: s.n.], 2012.

De Veylder L., T. Beeckman, and D. Inzé. The ins and outs of the plant cell cycle. *Nature Reviews Molecular Cell Biology*, v. 8, n. 8, pp. 655-665, 2007.

Machida Y. J., J. L. Hamlin, and A. Dutta. Right place, right time, and only once: replication initiation in metazoans. *Cell.* 123:13-24, 2005.

Masuda H. P., L. M. Cabral, L. De Veylder, M. Tanurdzic, J. De Almeida-Engler, D. Geelen, D. Inzé, P. C. G. Ferreira, R. A. Martienssen, and A. S. Hemerly. ABAP1 is a novel plant Armadillo BTB protein involved in DNA replication and transcription. *The EMBO journal*, v. 27, n. 20, pp. 2746-56, 22 out. 2008.

Morison J. I. L., N. R. Baker, P. M. Mullineaux, and W. J. Davies. Improving water use in crop production. Philosophical transactions of the Royal Society of London. *Series B, Biological sciences*, v. 363, n. 1491, pp. 639-58, 12 fev. 2008.

Parry M. A. J. and M. J. Hawkesford. An integrated approach to crop genetic improvement. *Journal of integrative plant biology*, v. 54, n. 4, pp. 250-9, abr. 2012.

Ramirez-Parra E., B. Desvoyes, and C. Gutierrez. Balance between cell division and differentiation during plant development. *The International Journal of Developmental Biology*, v. 49, 2005.

Sun J. and D. Kong. DNA replication origins, ORC/DNA interaction, and assembly of pre-replication complex in eukaryotes. *Acta. Biochim. Biophys. Sin.*, v. 42, n. 7, pp. 433-439. 2010.

What is claimed is:

1. A chimeric gene that increases biomass, yield, and/or drought tolerance in a plant transformed with the chimeric gene, the chimeric gene comprising the recombinant antisense nucleotide sequence of the full length nucleotide sequence as set forth in SEQ ID NO:3; wherein the chimeric gene further comprises a plant-expressible promoter operably linked to the recombinant antisense nucleotide sequence; wherein transcription of the chimeric gene in a plant cell produces the recombinant antisense RNA molecule of SEQ ID NO: 3 that reduces or silences expression of SEQ ID NO: 1 encoded by SEQ ID NO: 3; and wherein expression of the chimeric gene in the transformed plant results in increased biomass, yield, and/or drought tolerance of the transformed plant as compared to a control plant of the same plant species and grown under the identical growth conditions.

2. A transgenic plant comprising:
the chimeric gene of claim 1,
wherein expression of the chimeric gene results in increased biomass, yield, and/or drought tolerance in the transgenic plant as compared to a control plant of the same plant species and grown under the identical growth conditions.

3. Progeny and seeds of the transgenic plant of claim 2 comprising the chimeric gene.

* * * * *

SEQUENCE LISTING

```
<160> NUMBER OF SEQ ID NOS: 29

<210> SEQ ID NO 1
<211> LENGTH: 213
<212> TYPE: PRT
<213> ORGANISM: Arabidopsis thaliana

<400> SEQUENCE: 1

Met Glu Lys Gly Val Gly Phe Glu Lys Asp Met Lys Thr Val Ser Asp
1               5                   10                  15

Gly Phe Val Gly Gly Phe Phe Pro Val Ser Thr Thr Lys Ile Ala Trp
            20                  25                  30

Lys Ser Arg Lys Arg Ser Ala Leu Leu Asn Leu Asp Lys Ala Pro Glu
        35                  40                  45

Ala Val Thr Glu Val Thr Pro Glu Lys Asn Glu Ile Thr Ala Met Asp
    50                  55                  60

Thr Glu Lys Val Gly Glu Pro Met Thr Thr Pro Leu Leu Ser Glu
65                  70                  75                  80

Lys Arg Lys Ala Leu Phe Glu Pro Leu Glu Pro Ile Thr Asn Leu Asn
                85                  90                  95

Gly Lys Arg Pro Thr Ala Ala Asp Ser Leu Leu Pro Pro Asp Phe
            100                 105                 110

Glu Thr Ala Asn Tyr Pro Lys Gly Trp Leu Ile Gly Lys Lys Arg Lys
        115                 120                 125

Leu Val Asn Val Asp Val Val Glu Ser Met Arg Arg Ile Ala Val Gln
    130                 135                 140

Glu Met Asn Arg Lys Asp Arg Glu Ile Asp Gly Leu Asn Glu Gln Leu
145                 150                 155                 160

Glu Glu Asp Ser Arg Cys Leu Glu His Leu Gln Leu Gln Leu Leu Gln
                165                 170                 175

Glu Arg Ser Lys Arg Thr Glu Ile Glu Arg Glu Asn Thr Met Leu Lys
            180                 185                 190

Glu Gln Val Asp Met Leu Val Asn Met Ile Gln Glu Asp Asp Glu Glu
        195                 200                 205

Gly Ala Glu Glu Pro
    210

<210> SEQ ID NO 2
<211> LENGTH: 175
<212> TYPE: PRT
<213> ORGANISM: Arabidopsis thaliana

<400> SEQUENCE: 2

Met Glu Lys Gly Val Gly Phe Glu Lys Asp Met Lys Thr Val Ser Asp
1               5                   10                  15

Gly Phe Val Gly Gly Phe Phe Pro Val Ser Thr Thr Lys Ile Ala Trp
            20                  25                  30

Lys Ser Arg Lys Arg Ser Ala Leu Leu Asn Leu Asp Lys Ala Pro Glu
        35                  40                  45
```

Ala Val Thr Glu Val Thr Pro Glu Lys Asn Glu Ile Thr Ala Met Asp
    50                  55                  60

Thr Glu Lys Val Gly Glu Pro Met Thr Thr Thr Pro Leu Leu Ser Glu
65                  70                  75                  80

Lys Arg Lys Ala Leu Phe Glu Pro Leu Glu Pro Ile Thr Asn Leu Asn
                85                  90                  95

Gly Lys Arg Pro Thr Ala Ala Asp Ser Leu Leu Pro Pro Pro Asp Phe
            100                 105                 110

Glu Thr Ala Asn Tyr Pro Lys Gly Trp Leu Ile Gly Lys Lys Arg Lys
        115                 120                 125

Leu Val Asn Val Asp Val Glu Ser Met Arg Arg Ile Ala Val Gln
    130                 135                 140

Glu Met Asn Arg Lys Val Lys Gln Thr Lys His Asp Ala Asp Phe Cys
145                 150                 155                 160

Trp Ser Leu Ile Tyr Gly Leu Trp Asp Cys Asp Arg Ile Glu Arg
                165                 170                 175

<210> SEQ ID NO 3
<211> LENGTH: 1589
<212> TYPE: DNA
<213> ORGANISM: Arabidopsis thaliana

<400> SEQUENCE: 3

```
atacgataag acaactattt tcgacttctg atttttttc tttttgtaag aataaaaaac      60
attttcacaa gcctctgtag ctgaagcaca aagcaaaagc atttggtagt cgtaaccaaa    120
acgccaaatc attaccgttc aactgaaatc taacagagag ccctcttttc ttgggaattc    180
gattccttgt acgttatctt cttcttcttc ttctctttct caaaattcgt gtatcttctg    240
ggaaattttc agatttagat ggagaaaggg gttggatttg agaaagacat gaagacagtc    300
agtgatgggt ttgtcggagg ttttttccct gtctctacca ccaagatcgc gtggaaatca    360
agaaaaagat caggtttttt ccactgtttc ttgttttctc agaccattaa agattctaga    420
cctttattag ctacccttc tatttctggt ctgaaagatt tggaatttt tttaagcatc     480
aattgtttta gctctatgtg aactatttcc tcgagatcta gacatggagc tttagtcttc    540
ttctctctgt cttaagcttg taaaatcaaa gactttgtaa ctttcgtttt gatctgatcc    600
gtttgcatgt gattttggaa ctcaaagcat taactatttt gatcgcagca ttgttgaacc    660
tagacaaagc accggaggct gttacggagg tcacaccaga gaagaacgag ataacagcaa    720
tggataccga gaagttggg gaaccaatga ccacaactcc tcttctgtcc gagaaaagga    780
aagctctgtt cgagccactt gaacccatta cgaacttgaa cggaaagcga ccaactgcgg    840
ctgattcatt gttgccaccg ccggatttcg agactgcaaa ctacccaaaa ggctggttga    900
tcggtaagaa gaggaagctt gtgaatgttg atgtagttga gagcatgcgt agaatagctg    960
tccaagaaat gaacagaaag gtaaaacaaa ctaaacatga tgcagatttt tgctggagtt   1020
tgatttacgg attgtgggat tgtgacagga tcgagagata gatgggttaa acgagcagct   1080
agaagaggat tcacggtgct tagagcatct acagcttcag ctgctacaag agagaagcaa   1140
gagaacagaa ttgaaagag agaacacaat gttgaaagag caagttgata tgcttgtgaa   1200
catgatacaa gaagatgacg aagaaggagc tgaagaaccc taagctagtt ctcatcaaat   1260
ttatgtctca cctataatag ctgtgttctg tttttttat tcttttgtag atttgtctcg   1320
tccacaaaaa agaagaaaag aaagaagctt aaccatctat tatttggtta agctactctt   1380
```

```
gttcccttgt gtgatagaac aaaacataat caagaacatt atatattcta agttatgagt    1440
tctcctgcaa gatttgaacc tggcatttga ttgaatcgat tatgttcatt gaagctctta    1500
ggaggaaaaa gaaccatttg gtgtgtgtgt gtgtgtgtgt atctttcttc agcaagaaac    1560
agaggcaaaa taaatacaag tttcagaaa                                      1589

<210> SEQ ID NO 4
<211> LENGTH: 1201
<212> TYPE: DNA
<213> ORGANISM: Sorghum bicolor

<400> SEQUENCE: 4
agtacgccgt ttccgccatc gttaggcgtt acgtccctga aaggaaaacc caagccaacg      60
atgaccacga cgacagggcc aagaaacggg gagtgtattc caaggcgacc accgcccccc     120
tctcgcactc caaacagcac acgtccatcc gtcagcccag agccacaaga taacgcaacc     180
aacaagacac agcgagcgag cgagcgagga aagggagta gcgcgcgcgg cgcagcgcgg      240
caaccaggtc caggagaaag ggaagcccag ttagcctgga gccgagaagc cgccgaggga     300
gcgagggagc agccaggcat ggaggagccc gttccggctg atcccccag gattttctgg      360 aagtcaagga gatcagccaa tggccggagc ttgcaacaag aacctgacaa agatgctacc     420
gaagaaacta atgagcaggc tcaagaggaa cccatgaaga ccgacgatgc aacagataca     480
acagctacag ctgaggatgt acaaccagac ccaaaagcta acttatctga agcggaag       540 gctctctttg agcctcttga gccgatcaat ggaaagcgca gtgctgaaat gctgcttcca     600
ccaccggact ttgagcccgc atcatatcct aagggatggc tggtgggcaa gaaacgtaag     660
ctcgtcaatg tagatgttgt ggagagcatg aggaggattg caatccaaga aatgaacaga     720
aaggaccgtg agatcaatgg actgaacgag cagttagagg aagactcccg tgtgctggag     780
cttctacaga gcagcttgc cgatgagcgc aagaagcggg cagagattga aaggaaaat      840 tctatgcttc atgagcaggt gaacatgctg atgaacatgc ttgacgaaaa tgagggtttc     900
gatgaggacg gagaagctcc accgcccgat tcctttgatt aagcattaca ttactatcca     960
ttttccaaca atatcaagtc atacatctct aggtaccggt ttcagagtat ccaagggata    1020
tatgctgtgt agaatttcat ttatcgtatt ccattacatg gcttgtgttt ctgtagataa    1080
agagtgcatg tctgttgcac caactccttt ctaggcttca aatgtatgtg agaaactagt    1140
aacatattat atttgaatcg aagtgtatgt acatgttata tgaaattctt ccttgctatg    1200
c                                                                     1201

<210> SEQ ID NO 5
<211> LENGTH: 1088
<212> TYPE: DNA
<213> ORGANISM: Saccharum

<400> SEQUENCE: 5
aaacgggagt gtcttccaag gcgaccgccc cctctcgcac tccaaacagc acacatccat      60
ccgtcagccc agagccacaa gataacgcaa ccaacaagac acagcgagcg agagggcggg     120
gagaaaagag tagagcgcgt ggcgcggcaa ccaggtccag gagaaaggaa gcccagctag     180
cctggagcca agaagccgag ggagcgaggg agcagccagg catggaggat cccgttccgg     240
ctgatccccc caggattttc tggaagtcaa ggagatcagc caatggccgg agcttgcaac     300
aagaacctga caaagatgct accgaagaaa ctaatgagca ggctcaagag gaacccatga     360
agaccgacga tgcaacagat acaacagcta cagctgagga tgtacaacca gacccaaaag     420
```

-continued

| | |
|---|---|
| ctaacttatc tgagaagcgg aaggctctct ttgagcctct tgagccgatc aacggaaagc | 480 |
| gcagtgctga aatgctgctt ccaccaccgg actttgagcc cgcatcatat cctaagggat | 540 |
| ggctggtggg caagaaacgc aagctcgtca atgtagatgt tgtggagagc atgaggagga | 600 |
| ttgcaatcca agaaatgaac agaaaggacc gtgagatcaa tggactgaat gagcagttag | 660 |
| aggaagactc ccgtgtgctg gagcttctac agaagcagct tgccgatgag cgcaagaagc | 720 |
| gggcagagat tgaaaggaa aattctatgc ttcatgagca ggtgaccatg ctgatgaaca | 780 |
| tgcttgacga aaatgagggt ttcgatgagg atggagaagc tccaccgccc gattcctttg | 840 |
| attaagcatt acattactat ccgttttcca tcaatatcaa atcatacatc tctaggtacc | 900 |
| ggtttcagag tatccaagag atatatgctg tgtagaattt catttatcgt attccattgc | 960 |
| atggcttgtt ttctgtagat aaagggtgca tgtctgttgc acgaactcct ttctaggctt | 1020 |
| caaatgtatg tgagaaacta gcaacataat atatttgaat cgaagtgtat gtacatatta | 1080 |
| aaaaaaaa | 1088 |

<210> SEQ ID NO 6
<211> LENGTH: 1221
<212> TYPE: DNA
<213> ORGANISM: Zea mays

<400> SEQUENCE: 6

| | |
|---|---|
| agtacgccgt ttgcgccatc gttacgtcca ccagaaggaa aacccaagcc aacgacgacg | 60 |
| gcacggccaa gaaacgggga gtgccttcca aggcgaccgc cccctctcgc gctccatacg | 120 |
| tccatccgtc ggcccagagc cacaagataa cgcagccaag aacaagagac accgccgagc | 180 |
| gagcgaggcg gggagaagca ggtccaggac caggagaaag gaaaaggaag cccagctctc | 240 |
| tctagcctgg agccgagaag ccgaggggc gaaggagcag caaggcatgg aggagcccgt | 300 |
| tccggctgat ccccccagga ttttctggaa gtcaaggagt tcaggttcag ccaatggccg | 360 |
| gagcctgcaa caagagcctg acaaagacgc taccgaggaa actaacgagc aggctcaaga | 420 |
| ggaacccatg aagaccgacg acgcaacgga cacagcagca gcagcagcag ctacagctga | 480 |
| gccgtacccg aaagctaacc tatccgagaa gcggaaggct ctcttcgagc ctctcgagcc | 540 |
| gatcaacggc aagcgcggcg ctgctgagac gctgctccca ccgccggact ttgagcccgc | 600 |
| gtcgtacccc aaggggtggc tggtgggcaa gaaacgcaag ctcgtcaacg tagacgtcgt | 660 |
| ggagagcatg cggaggattg cgatccagga aatgaacaga aaggaccgtg agatcaatgg | 720 |
| gctgaacgag cagctagagg aagactcccg cgtgctggag cttctgcaga agcagctggc | 780 |
| tgacgagcgc aggaagcgga cagagatcga aaggagaaac tccatgctcc atgagcaggt | 840 |
| caccatgctg atgaacatgc tcgacgagaa cgagggtttc gacgaggacg agagggcccc | 900 |
| gccgccgat tccttcgatt aagcgttgtt acagtactat atccgtttc ttttcccgt | 960 |
| cagtgtgaaa tcatacgtct ctaggtgctg gtttcagagt atccgagaga tatgggctag | 1020 |
| ctgtgtagta ggatttcatt ggtggtcgta ttccattaca tggctttggc ttctgtagat | 1080 |
| aaagggtgca ttgcatgtct gttgtactgt actgtaccta ctccttttct aggcttcaaa | 1140 |
| agtgtatgtg agaaactagc aacatgttat gtttgaatcg aagtgtatgt acatgttact | 1200 |
| taaaattctt ccttgctatg c | 1221 |

<210> SEQ ID NO 7
<211> LENGTH: 744
<212> TYPE: DNA

<213> ORGANISM: Theobroma cacao

<400> SEQUENCE: 7

```
atggagaaag agaacaagaa ggtagatgca gcagctttgg aagggttttc tcctgtcact    60
acaactagga ttttctggaa atccaggaag agatcaggta gtgtcagttc tttgttttca   120
cttttctctgc ttggtttcta tggaaatgaa gcatcaattg agctcccttc atggtggcat   180
cctttcaatg ggtttagtaa aacagagaac actagcggga ggaatttaga caaggtaaca   240
gaagagactg ctaatatgac acccaccaaa caggaagaag aaactccaga tcaagagaat   300
gccccagatc caacaacagc ttctgaactt tctgagcgcc ggaaggctct ctttgaacca   360
ctggaacccca taaaaatct caatggccag cgcccatcag ctgaatcttt acttcccca   420
ccagactttg atgctgcaat ctatcccaag ggctggctga ttggaaagaa gaggaagctg   480
gtaaatgttg atgttgttga gagcatgagg aggattgcag tccaggaaat gaacagaaag   540
gaccgggaaa ttgatggcct aaatgagcag ttggaagaag atgcccgatg cctagaacat   600
ctgcaacttc agcttttaca agagaaaagt aaaaggtcag acgtagagag agaaaatgca   660
atgcttcaag aacagatatc catgctgatg aacatgttgc aggagaacga agcatggga   720
gacgaaggtc cagatgaagc ttaa   744
```

<210> SEQ ID NO 8
<211> LENGTH: 1143
<212> TYPE: DNA
<213> ORGANISM: Phaseolus vulgaris

<400> SEQUENCE: 8

```
gtaagttgtt tgggagaagg aaaacgagac ttttagatgg tcggaagatt aaggtaaaaa    60
ccaaacagca cctccaaaaa acaacacaac acaacacaaa acctttctct ctctttctct   120
tctctttgtt ttagtatgtg ttgaaattct gaatttgaag catatcttgt tcttgaatgg   180
aaaacatgaa gatgtccata gatgatgctt tgaacgcctt ctctcccgta tccacagcta   240
ccatttactg gaaatcccga agaagaccag ctagcgggag gaatttagag gtatcagaag   300
atactgctaa tacaccaccc agcaagcagg aagatactcc tcctcctcct ccttcttctt   360
ctagtgagga ggtgcagaac acaactccaa tttctgagcg tcgaaaggcc ttgtttgaac   420
ctttagaacc tataaagaat gttaatggcc gacgaccctc ggctgagtct ttacttcctc   480
cccctgactt tgagtctgca aactatccta agggctggct gattggaaag aagcggaagc   540
ttgttaatgt agatgttgtt gaaagcatgc gaaggattgc catccaagaa atgaacagaa   600
aggacaggga aattgatgga ctaaatgaac aactggagga ggattcacgt tgcctggagc   660
acttgcaact tcagcttgtg gatgaacgaa gcaaacgtgc tcgagttgaa agagagaatg   720
caatgcttga gaacaagtg agcatgctta tgaacatgtt acaagaagca gaacaaatgg   780
gagatgaagg cccagatgaa ccttaatgtt tatcattaca cattttgtgt gcttgtgtgt   840
atcaatttttt tgtgtgtatc aattttttgt gtgtaggttc tgttcgtcat gtctagcata   900
ttggatgtct atgcagttat tagagtgctt gtagtaatat ctgggggcaa atagatcaaa   960
tcgcaatgag caaactattc gtttgtctct aaaaaaaagt tgtaattctt tctagagact  1020
atgtggttgt taattcatat cttgttactc tttcaaacta taaagagta ttgtaattta  1080
tctacttgcc aagtttataa agtggctcag ttgaataaag atctcggttc aataagatca  1140
tag                                                                 1143
```

<210> SEQ ID NO 9
<211> LENGTH: 1201
<212> TYPE: DNA
<213> ORGANISM: Oryza sativa

<400> SEQUENCE: 9

| | | | | | |
|---|---|---|---|---|---|
| gaaggcacgc | gagacggtca | agaaacaaac | gggagttgct | tccaaggcga | aggcgacccg | 60 |
| gtgacccacc | tctcctctct | cttctcgccg | tcctagcaag | tagcaaccct | cctcagccaa | 120 |
| gaaccacaag | ataacgcaac | tcacaaggca | cgcacccata | gattgataga | gagagggaca | 180 |
| gagagagaga | gagatagagc | tcaggttgca | agcagataga | acgggtccag | gtagcttcgc | 240 |
| aatcaagaag | aagaagaaga | gtgaaggagg | aggaggagca | agagcaagcc | atggaggagc | 300 |
| cggcctcggc | tgatccccg | cggattttct | ggaagtcgag | gaggagatca | gcctcagcca | 360 |
| atggccggag | cttgcaacaa | gaacttaaca | aagaggctgc | tgatgaacaa | ctgaacaatc | 420 |
| aggctcatga | agaggccatg | aaaatagatg | atgcaaatgc | agtaagtact | gacgacgatg | 480 |
| ttcatccaga | tccaaaagct | aacttatctg | agaagaggaa | ggcgctgttt | gagcctttgg | 540 |
| aaccaatcaa | cggcaagcgc | agttctgctg | aaatgttgct | cccaccacca | gactttgagc | 600 |
| ccgcgtcata | tcccaaggga | tggctggttg | gcaagaaacg | caagcttgtg | aatgttgatg | 660 |
| tggtggagag | catgaggagg | atagcaatcc | aagaaatgaa | cagaaaggac | cgtgagatca | 720 |
| atggcctgaa | tgaacagttg | gaagaagact | cccgagtgct | tgagcttcta | caaaagcagc | 780 |
| tcgcagatga | gcgtaagaag | cgaacggaga | tagagaagga | aaattccatg | cttcatgagc | 840 |
| aggtatctat | gctgatgaac | atgctcgatg | aaaatgaagc | cttttgatgag | gagggagaag | 900 |
| caccaccacc | tgatacctta | taggcttaga | ttaagtaata | ttatcaaggt | tccaagttct | 960 |
| acacatcttc | ggataccagt | ttaagagtat | tcccagatgt | ctttatcttg | tgtaaaattc | 1020 |
| aatttatctt | atttattttt | atggcttgtg | tgtagatgaa | ggggttctgt | ttgctgtacc | 1080 |
| tatttgtttc | taggctgcaa | gtgtatgcga | gatgcttgta | atgtattcta | tttaaatgca | 1140 |
| agtgtttaca | tgttataaga | gctcttgcaa | gactccttt | ccttgcatga | gctcttttgc | 1200 |
| t | | | | | | 1201 |

<210> SEQ ID NO 10
<211> LENGTH: 1071
<212> TYPE: DNA
<213> ORGANISM: Vitis vinifera

<400> SEQUENCE: 10

| | | | | | |
|---|---|---|---|---|---|
| gaaagcttta | caacaaggaa | caaaggaaca | agaaaaagaa | ggaacaagga | taattctgag | 60 |
| aattccaact | tgcccaactc | acctcctcgc | ttcttctctt | catttctctc | tctctctctc | 120 |
| ccctctctc | cttcaatgga | ccttcccaag | aagcctgacg | ggaaccttga | tggcttctcc | 180 |
| acagtctcct | cctccacaag | ggttttctgg | aattccagaa | ggagatcagg | aagcgggcgg | 240 |
| aatttagaaa | aggttgcaga | agataccagt | gataatacac | ccaaaaaaca | ggatgaatct | 300 |
| ccgcctgaag | agacgatgca | ggacatttct | gttttatctg | agcgtaggaa | ggctctttt | 360 |
| gaaccattgg | aacctttaac | tgggtcacga | cccttagccg | aatccttgct | gcctccacct | 420 |
| gacttcgact | ctgcaaacta | tcctcgaggt | tggctgatag | aaagaagag | gaagcttgtg | 480 |
| aatgtggatg | ttgttgagag | catgaggaga | attgctgtcc | aggaaatgaa | tagaaaggac | 540 |
| cgggaaataa | atggcttaaa | tgggcagtta | gaagacgatg | caaggtgctt | ggaacacctc | 600 |
| caagtccagc | tcctgcaaga | acgcagcaaa | cgtgcagagg | tagaaagaga | gaacttgatg | 660 |

-continued

| | |
|---|---|
| ctgaaagatc agttgtctat gctgatgaac atgttgcagg aacaggaggc aatggaaaat | 720 |
| gagagcacag aagagcatta aaattgttgt gttgctttgt ctgtttaatt cttttgtata | 780 |
| tctattcgtg ggttcggaaa cgaagaacca ccatagaacc ataccgtata tactaggatt | 840 |
| gccaatgtag tttcttggtg ctacaagtag cttgcatttg ttattgtttg taattgagtc | 900 |
| tttaatatct tgttaaagta ttaagtttgg gtaaattgta tcttatctgt gtgtgtatat | 960 |
| ttgccaacaa caacaaccag ctcaaacaag gctgtgttgt tgagacaact caaagtgaaa | 1020 |
| actcctattt gccagatgat ataaaggatc atcatcttct ttgttgtgtc a | 1071 |

<210> SEQ ID NO 11
<211> LENGTH: 3145
<212> TYPE: DNA
<213> ORGANISM: Solanum lycopersicum

<400> SEQUENCE: 11

| | |
|---|---|
| aaacaaaaaa ggggctcaag agttggatgg aggtaaggca gcagcagaag atggaaggat | 60 |
| ttcttgaggg attttcacct gtttcttcaa ctcctgtttt atggaagtct agaaaaagat | 120 |
| ctggtaaggc agcagcagaa gatggaagga tttcttgagg gattttcacc tgtttcttca | 180 |
| actcctgttt tatggaagtc tagaaaaaga tctggtaata tttctttgtt cttttttctct | 240 |
| gattttcaat ttagtactag tattgcatgt agctacagtg atttattgaa atatggggtt | 300 |
| gattattgt gctataacta gatctatttc tagaaatgat tagaaaatac gcagcaaagc | 360 |
| tagaatttga agtttcgatt atagtcattt taagtcgttg agttctgaat taatggtttt | 420 |
| attagttgtt gggtttcaca gtttccggtt aagttgaaag tagaggataa ttttgtccaa | 480 |
| tattagctag atttagtggc gaatttgccg acacgtcatt tctagctaat aaataagttc | 540 |
| gattttcgaa taaaaacat tttttttttt tttgtaaatt tatccgtagc ttattaggta | 600 |
| accattaata aagcatcgat ttttagtgat tttggttgtc tttgtcatga tgagtgtgtt | 660 |
| ttgattcatt cattacatta catgtttctt ctgcataatt ttacttattt gttaaggaat | 720 |
| ttgcctgtat aagctaaact tgattaccac tccaatattt tattttcaa agactaatct | 780 |
| attattccac accggatatt gtgtagaaat agtgatttgg ccctgcattg ttgactttgt | 840 |
| attttttta atgtacatgt tcttttccc ttaagcggac tccttaatt atttggaaat | 900 |
| tcttcgagat ggattagaat atgaaagatg acttgtggag ctttagaaag actgattgaa | 960 |
| aagaaaaaag atccttttct aagaaaggtt acatataata taattaaa gacggtataa | 1020 |
| tcattccata attacagagg tcgaaacaaa tgtgttaga tagaatctca aactcgaatc | 1080 |
| tgaaaagttt aaatcttgga tccaccttg ctcgatagtg ttttgtgaa tgctacatca | 1140 |
| aatagcagac ttgtttcttc actgatcaag gagaagattt gtagttagtg agctttttaa | 1200 |
| ttacacaaga ctggctcatg ctatttgaac ttgaaccagt caacaatttt cgttgagtcg | 1260 |
| aaggtctatc agaaacagtc tctctacctc ccaaggtgta ggggtaaggc ttgcgtaacc | 1320 |
| ctccccagac cccacttatg gatttatatt gggtatgttg tagttgttga aatagtcaac | 1380 |
| aatttctgaa catcactaat attttgtttg gagaacatac ttctgatatt ttagtcctgt | 1440 |
| ttaatgtctt gttccataaa gataatagag tgatgactat aagcccaatc aatacacagt | 1500 |
| tcatacaatt catattttgt atatcataca tttatcatgc taaggaaatg cttcgcctag | 1560 |
| tagccggtgt gaagaacttg gaaacgcctc aaaagcaaga agagtctcca gctgatgaaa | 1620 |
| cacctcaaaa gcaagatgag tctccagctg atgaaagat gcaggaatcg cagccctcta | 1680 |
| ctgaactttc agagcgtagg aaggcactct ttgaaccatt ggagccggtt acaaatgcaa | 1740 |

```
atggccgtag ccatcagct gaaactttgc taccccccacc agactttgat gctgcatgtt      1800 acccccaaagg ttggctggct ggaaagagac ggaagcttgt aaatgtggat gttgttgaaa      1860
gtatgcgaag aatcgctcta caggaaatga atagaaaggt aatgtcctca aaattaccat      1920
ttgtttactt tcttctaatc tacatgtttt gttttggcta aagctcttaa aatgtcttgc      1980
tcagtttaaa ttcaacagaa acactaacca tatgacaatg ctgcaggatc gcgaaatcga      2040
tggtctgaat gaacagctag aagcagatgc tcaatgcctg aacatctgc aaatacagct       2100 gctagaagaa agaagcaagc gtgctgatgt agagaggcaa aatgctatgt tgcaaagcca      2160
gataaatgtg cttatgaaca tgtatcagga tgacgatgat attgatggtg acggtacaga     2220
tgactcttaa tcagtcattt tctttattct tttgtagatt tcgttagaca ataataggac      2280
agatatagaa gaaggttgtt gtgctttcaa gatgtaaaat atatatttgc gagtaccacc      2340
tgtgtgttcg caatattatt tactgtttaa aagctgtgta agacgttggt agttccttt      2400 atttgatcca tcattccggt gtgaagaact tggaaacgcc tcaaaagcaa gaagagtctc      2460
cagctgatga aacacctcaa agcaagatg agtctccagc tgatgaaaag atgcaggaat      2520
cgcagccctc tactgaactt tcagagcgta ggaaggcact cttttgaacca ttggagccgg    2580 ttacaaatgc aaatggccgt aggccatcag ctgaaacttt gctaccccca ccagactttg     2640
atgctgcatg ttacccccaaa ggttggctgg ctggaaagag acggaagctt gtaaatgtgg    2700
atgttgttga agtatgcga agaatcgctc tacaggaaat gaatagaaag gatcgcgaaa      2760
tcgatggtct gaatgaacag ctagaagcag atgctcaatg cctggaacat ctgcaaatac     2820
agctgctaga gaaaagaagc aagcgtgctg atgtagagag gcaaaatgct atgttgcaaa    2880
gccagataaa tgtgcttatg aacatgtatc aggatgacga tgatattgat ggtgacggta    2940
cagatgactc ttaatcagtc attttcttta ttcttttgta gatttcgtta gacaataata    3000
ggacagatat agaagaaggt tgttgtgctt tcaagatgta aaatatatat ttgcgagtac    3060
cacctgtgtg ttcgcaatat tatttactgt ttaaaagctg tgtaagacgt tggtagttcc    3120
ttttatttga tccatcattc ctcgc                                           3145
```

<210> SEQ ID NO 12
<211> LENGTH: 1278
<212> TYPE: DNA
<213> ORGANISM: Glycine max

<400> SEQUENCE: 12

```
aaaaaaaga caaggaaagg aaggaagtag aaatggtcca cacacagagg acacaaaaaa       60
attccaccga aacaagaaat ctggaccgtt gaaaattgtc aggttcatcg tgatggtccc     120
atacgagagc tttagatggt gggaagatga aggagaaagg caaagagcac ctccaaaaaa    180
aacaataacc gtagcccaca cctcctctca gcaaacatct ctctttctct gtttcttta     240 ttatgttgtg ttccttgggg gtgctgatgt atgtgtgttg aagttctgaa tttgaatgga    300
aacacgtgct agtggtgata tgaagatggc catagatgat gctttgaatg cttctctcc     360 tgtctccacc cctaggattt tctggaaatc acgaaggaga tcagctagcg ggaggaattt    420
agaggtatca gaagatactg ctaataaacc acccagcaag caggaagata ctcctccacc    480
ttctagtgag gaggtgcaga acacgactcc gatttctgag cgccgaaagg ctctgtttga    540
acctttagaa cctataatga atattaatgg ccgacgaccc tcggccgagt ctttactcc     600 tcctcctgac tttgagtctg caaactatcc gaagggctgg ctgattggca agaagagaaa    660
```

```
actcgttaat gtcgatgttg ttgaaagcat gagaaggatt gccatccaag aaatgaacag      720
aaaggacagg gaaattgatg ggctgaatga acagctggag gaggattcac ggtgtctaga      780
gcacttgcaa ctccagcttg tggatgaaaa aagcaaacgc gctcgagtgg aaagagaaaa      840
tgcaatgctg caagaacaag tgaacatgct tatgaacatg ttgcaagaag cagaacaaat      900
gggagatgaa ggcccagatg aaccttaaag tttattatta taccgtgtgt gtgtgtgtgt      960
gtgtttgctt gtgtgtatta aattctttt gtaggttttg ttcgtcatgt ctagttggct     1020
gcgcatgtcg gatgtctctg cagttataaa aatagagtgc atatattaat atttgtgggg     1080
aaatagatca aaccgcaatg agcaaactat tcgtttatat caaaacaaaa caaaacaaaa     1140
cttgtaaatc ttctggtgac catgtggttg ttagtttata tcttgtaagt cttttaacct     1200
ataaaatagt attttaattt tagatacttt ccaagttgat tcagtggctc agttaaataa     1260
agatcacagt cgagatta                                                   1278
```

<210> SEQ ID NO 13
<211> LENGTH: 1226
<212> TYPE: DNA
<213> ORGANISM: Glycine max

<400> SEQUENCE: 13

```
acataaaaat ttccaccgaa acaagaaatc aggaccgttg aaaaaagctg aagctcatca       60
tgatggtccc atacaattat cagcatctgc gtgtgagttg ttagagacaa gaaaaacgag      120
acctttagat ggtcggaaga tcaaaaggag aaagccaaac agcacctcct cagcaaatta      180
acataaaaaa cctctctttc tctatttctt ttattattgg gtatgtcttg aagttcttct      240
gaatttgaag catatatttg tccttgaatg gaaacacgtg ctggaagtga tatgaagatg      300
gccatagatg atgctttgaa cgccttctct cctgtttcca cccccaggat tttctggaaa      360
tcacgaagga gatcagctag cgggaggaat ttagaggtat cagaagatac tgctaataaa      420
ccacccagca agcaggaaga tactcctcct cctcctcctc caccttctag tgaggaggtg      480
cagaacacga ctccgatttc tgagcgccga aaggccttgt ttgaaccgtt agaacccata      540
atgaatatta atggccgacg acccttggct gagtctttac ttcctccccc tgactttgag      600
tctgcaaact atccaaaggg ctggttgatt ggcaagaaga gaaagcttgt taatgtcgat      660
gttgttgaaa gcatgcgaag gattgccatc caagaaatga acagaaagga cagggaaatt      720
gatgggctaa atgaacagct ggaggaggat tcacggtgtc tagagcactt gcaactccag      780
cttgtggata aaaaagcaa acgtgctaga gtggaaagag aaaatgcaat gcttcaagaa      840
caagtgaaca tgcttatgaa catgttacaa gaagcagaac aaatgggaga tgaaggccct      900
gatgaacctt aaagtttatt attatacccca gtgtgtgtgc ttgtgtgtat taaattcttt      960
ttgtaggttt tgttcgtcat gtctagttgg ctgcgcatgt cggatgtctc tgcagttatt     1020
aattagagtg tgcatatagt aatatttggg gggaaataga tcaaaccgca atgagcaaac     1080
tattcgttta tctcaaaaaa aaaaaaaaat tgtaaatctt ctggtgactg tgtggttgtt     1140
aatttattat atcttgttac tcttttaagc tataaaagag tattgtaatt tagatacttt     1200
ccaagttgat tcagtggctc agttaa                                         1226
```

<210> SEQ ID NO 14
<211> LENGTH: 693
<212> TYPE: DNA
<213> ORGANISM: Manihot esculenta

<400> SEQUENCE: 14

```
atgaatctaa gtaggctgaa ctcctctgct atggaaaaga agaaagatta cagtaataag    60
gatgggaaga aggtgttgga tgggcttta  gatggcttct ctccagtctc tacgcctaga   120
atcttttgga aatctcgaag gagatcagct agcgggagga atttagacaa ggtaacagac   180
gatacagcta agaaactcc  tagcaaacag gaagaaattt ccaatgatga agacatgcag   240
gagcccaaag aacttccaga actctcagaa cggcgaaaag ctctctttga accattggaa   300
cctgtgacaa atatcaatgg aaaacgacct tcagctgaat cccttctacc tccacctgat   360
tttgactcag caagctatcc caagggttgg ctaattggaa agaagcggaa gcttgttaat   420
gtagatgttg ttgagagcat gagaaggatt gctgttcagg aaatgaacag aaaggaccga   480
gagattaatg gcctaaatga gcagttggaa gaggatgcga ggtgtttaga cacctgcaa    540 ctccagcttc tccaagaacg aagtaaacgt gctgaggtag agagagagaa tgctatgttg   600
cacgaccaaa tatccatgct gatgaacatg atagaggaaa atgaacaaat gggcgatcaa   660
ggtgccacag atgagggccc tgatgagcct taa                                693

<210> SEQ ID NO 15
<211> LENGTH: 495
<212> TYPE: DNA
<213> ORGANISM: Manihot esculenta

<400> SEQUENCE: 15
atggaagaat cttccaatga tgaaaagatg caggagccag atacacttcc tgtgctttct    60
gagaagcgaa aggctctctt tgaaccattg gaaccagtaa ccaatatcaa tggcaaacga   120
ccatcagccg agtcccttct tcctccacca gattttgact cagcaagcta tcccaaaggt   180
tggctaattg gaaagaagcg aaagcttgtt aacatagatg tcgtcgagag catgaggagg   240
attgccattc aggaaatgaa cagaaaggta tttgcttccc attcattgca ggaccgggaa   300
attaatggcc taaatgagca gttggaagag gatgcaaggt gtctagaaca cctgcaactc   360
cagcttctgc aagaacgaag taaacgtgcc aatgttgaga gagagaacgc aatgctgcaa   420
gaccaaatat ccatgctgat gaacatgcta gaggaaaatg aacaaatggg tgatgaaggc   480
cctgatgaac cttaa                                                    495

<210> SEQ ID NO 16
<211> LENGTH: 693
<212> TYPE: DNA
<213> ORGANISM: Ricinus communis

<400> SEQUENCE: 16
atgaagcttt caagaagtgc ttctttaatg gaaaaggata agaagtacga tagtaaacaa    60
gggaagaagg tcgatgatgg gctttttgaat ggattctcta tatcctctac tcctaatatc   120
tcctggaaat ctagaaggag atcagctagt gcgaggaatt ctgacaaggt aacaaacgac   180
actgctaatg aaacaccacc cgacaaacag gaagaatctt acaatgacga aaagatggag   240
gagctaaatg cagttccagt gctttctgag aagcggaagg ctctctttga accactggaa   300
cctgtaaaca atatcaatgg ccggcgatca tcagctgaat ctctgctccc cccaccagat   360
tttgatgccg caagctatcc aaaggggtgg ctgattggaa agaagcgtaa gcttgtcaat   420
gtagatgttg tcgagagcat gcgaaggatt gctgttcagg aaatgaacag aaaggaccgg   480
gagattgatg gcctaaacga acaattggaa gaagacgcaa ggtgtctaga gcacctgcaa   540
gtacagcttc tgcaggagcg gagtaaaaga gcagaggtag aaagagaaaa taccatgctg   600
```

```
caagaccaag taaccatgct gatgaacatg ctgcaggaca acgagccaat gggtgatgaa        660
ggcgcaggag atgaaggtcc tgatgaacct taa                                     693

<210> SEQ ID NO 17
<211> LENGTH: 456
<212> TYPE: DNA
<213> ORGANISM: Carica papaya

<400> SEQUENCE: 17
atgctgatac caccactgat gtgcctgtta aactggagct ttctgatcga cgaaaggctc         60
tgtttgaaac ctttagaacc tctgggaaat attagtggtc gtggaactca gccgaatcct        120
ttactacctc caccagactt cgactctgct gcatacccga aaggttggct cattggaaag        180
aagcgaaagc tagttaatgt ggatgtggtt gagagcatgc gcaggattgc tattcaggag        240
atgaacagaa aggatcggga aatagatggt ctaaatgagc agttagaaga ggattcgagg        300
tgcttacaac atttacagct tcagcttctg caagaacgaa gcaaaagtgc agatgtagaa        360
agacaaaaca aaatgctgca agagcaggtg tctatgctta tgaatatgtt acaagaacca        420
gtgatagtgg aggatgaagg cacagatcaa gcttaa                                  456

<210> SEQ ID NO 18
<211> LENGTH: 1065
<212> TYPE: DNA
<213> ORGANISM: Populus

<400> SEQUENCE: 18
cagcaaacaa aatacaagaa aagaaaaggt tgaaacagac acagcttgct atcttcaata         60
ccaaagaaac ctctccctcc ctccctccct ctccctctct gtatagaagc aaagagagag        120
cttggtgttc tagcaagttg acataacttc tttaatggga aggagaacg ataataatat         180 caaggatatg aagatggttg aagcagaacc tttgaatggc ttctctccag tctcttcaac        240
tagggtcttt tggaaatcta gaagagatc agctagcggg aggaatttag acaaggtaac        300
ggagaacact gttaatgaaa cacccaacaa acaggaagaa tcttccactg atgaaaagat        360
ggaggacccg aatccagctt cagagctttc tgagcgtcga aaggccctct ttgaaccatt        420
ggaacctgta acaaatatca acggcaaaag gctacctgca gaatccctac tccctccacc        480
ggattttgat gctgcgagct atcccaaggg ctggctgatt ggaagaagc gaaagcttgt        540 taatgtagat gttgttgaga gtatgaggag gattgccgtg caggaaatga atagaaagga        600
ccgagaaatt gatggcctaa atgagcagtt ggaagaagat gcacggtgtc tagaacatct        660
ccaacttcaa cttctgcaag aaaaaagtaa acgcaccgag gtagagagag agaatgctat        720
gctgcaagac cagatatcaa tgctgatgaa catgcttcag gaaaatgaac aattgggcga        780
cgaagatgtg ggcgatgaag accctgatgg accttaaata gttgtttgat cgtttatttt        840 ttcttttgt aggcttgttt ggaaagttag aagaatttat acatgaatac ttacacgttt        900
ttgtccacat atttctttgc ggtatttgtt accttatatg ttggaactgg tcgcaccttg        960
tgcacgcttc ttgttgttta tagttgtctc cttcctgtct tgtaaatgta tatatgcttc       1020
tggtaatttg ttcatgtgcc ttggctagca atgtttagat tcgat                       1065

<210> SEQ ID NO 19
<211> LENGTH: 2283
<212> TYPE: DNA
<213> ORGANISM: Populus

<400> SEQUENCE: 19
```

```
gaaacggaca ctctgcttgt tatctatctt catttccaca agaacctctc cccgtctgtc      60
tctctctcta taagcaaaga gagaccttgg tgttcatagt tcttgaaagt tgaagaaagt     120
tttcatcttc ttcaatggaa aaggaggacg ataataataa aaccaaggat gtgaggatgg     180
ttgaagttga accttttgaat ggcttctccc cagtctcttc aactaggatc ttttggaaat    240
ctagaaaaag atcagctagc gggaggaatt tagacaaggt aaccgaggac aatgttaatg     300
aaacacccaa caaacaggag gaatcttcca atgatgaaaa gatgcaggac caaaatctaa    360
ctccagagct ttctgagcgt cgaaaggccc tctttgaacc gttggaacct gtaacaaata    420
tcaatggcaa gagatcatct gcagaatccc tactccctcc tccagatttt gatgctgcaa    480
gctatcccaa gggctggcta attggaaaga agcgaaagct tgttaatgta gatgttgttg    540
agagcatgag gaggattgcc gtgcaggaaa tgaacagaaa ggaccgagaa attgatggcc    600
taaatgagca gttggaagaa gatgcacggt gtctagaaca tctccaactc caacttctgc    660
aagaaaaaag taaacgtgct gaggtagaga gagagaatgc tatgctgcaa gaccagatat    720
caatgcttat gaacgtgcta caggaaaatg agccaatggg cgatgaagat ctggggaatg    780
aaggtcctga tgaaccttaa atatgttttg attatttatt cttttttgtag gtttgttggg    840 gaaagttaga agaattcata catgaacata cacgcggttt tgtccaaata tttgttggag    900
gtcatgttac tgtatctgtt gaaatgggcg caccttgtgc acgcttgttg ctgtttgtag    960
tcgtgtctcc ttcctatctt gtaaatgcat acaggcctct ggtaatttgt tcatgtgttg    1020
atgcctcgtg gctaacaata tttagatcaa ttatgtggct agcaattctt ctgcccttt    1080 gttgcgctcg caattctgat tcatctttcg ctggttactt tgacagcaaa tcctgtccta    1140
cccattttgg catgcgctct gtgtggtttc atgtggcata ttttatctc ctggtttcca    1200 gtaaaaggca tgctgccact atagccgcca tcaaggatgt tttttctcaa agtcctagaa    1260
aaatgagcaa gaaattgtta tcctgattta tgtgcccctt ggacaaggtt gcatagaaag    1320
tgctctacga ttgaaaacgc tgccaacacc acattccacg tgcactatta gggctacaaa    1380
aggttgtgat cccctacaaa caccaagctt tacataaact gttaagattg caaaaggttg    1440
aacaaagaaa acactagttc aaacactatg gacaccagta tccccatatg aacatccgag    1500
gattcttcat caatatccat ttctgaatcc ccgagctgta caagttgaaa gaggcaaatt    1560
atatcactat accgcttcat tttcacaatc ttcctatata ttgaataaaa attgtggcag    1620
agaagcaata cttggaagat taagaagtag ctctccaacc gagtccttcc ttgacatggc    1680
tggtgcctgc ttgcaaatgg aaacattact ggcctctccc tcaggtgcgg gaaaactctc    1740
tataaatttg ctttgacacg cagatgcagt ggaattagtt tcgtttattc tcctatcatg    1800
atccacatca agatcgctga gactctttgc ctgcaagtcc cgagctgttg caggatcctt    1860
ctgcagtagg cagcaaagag aattgaccgt tgacacaacg gattgctcat ccgaggctga    1920
cataacttga gagtctccaa gcaagtattg agtaatttca tctagaatgt cactgctctt    1980
tatgtcacca ccagagagga tagaatttcc agaggtcatc tgttctgaaa tgcaatgtcc    2040
aatgtggttc acaaggtcgc tcattgaaat ggatggatga agtccgggca ctttaatttg    2100
atcacaattg cttggcaact gctgttctcc tgttctgttg ctcctggttt cttcaaatgc    2160
atgggtttcc attactagaa atgagaggca agttagaaag attacagtag gcaagataaa    2220
gagtttaaaa acattgcaaa taaatccaca agtgttccat tccagatact gatcttaata    2280
atg                                                                 2283
```

```
<210> SEQ ID NO 20
<211> LENGTH: 214
<212> TYPE: PRT
<213> ORGANISM: Gossypium raimondii

<400> SEQUENCE: 20

Met Glu Lys Glu Glu Lys Lys Lys Met Glu Val Asp Ser Ala Pro
1               5                   10                  15

Ala Ala Ala Leu Glu Gly Phe Ser Pro Val Ser Thr Thr Arg Ile Phe
                20                  25                  30

Trp Asn Ser Arg Lys Arg Ser Ala Ser Gly Arg Asn Leu Asp Lys Val
            35                  40                  45

Thr Glu Glu Thr Ala Asn Val Thr Pro Thr Lys Gln Glu Glu Gln Thr
    50                  55                  60

Leu Asp Gln Asp Asn Thr Pro Asp Ser Ala Thr Ser Ser Glu Leu Ser
65                  70                  75                  80

Glu Arg Arg Lys Ala Leu Phe Glu Pro Leu Glu Pro Ile Lys Asn Ile
                85                  90                  95

Asn Gly Arg Arg Pro Ser Ala Glu Ser Leu Leu Pro Pro Asp Phe
                100                 105                 110

Asp Ala Ala Ser Tyr Pro Lys Gly Trp Leu Ile Gly Lys Lys Arg Lys
                115                 120                 125

Leu Val Asn Val Asp Val Val Glu Ser Met Arg Arg Ile Ala Val Gln
    130                 135                 140

Glu Met Asn Arg Lys Asp Arg Glu Ile Asp Gly Leu Asn Glu Gln Leu
145                 150                 155                 160

Glu Glu Asp Ala Arg Cys Leu Glu His Leu Gln Leu Gln Leu Leu Gln
                165                 170                 175

Glu Lys Ser Lys Arg Ser Glu Val Glu Arg Glu Asn Ala Met Leu Gln
                180                 185                 190

Glu Gln Val Ser Met Leu Met Asn Met Leu Gln Glu Gly Glu Glu Gly
                195                 200                 205

Pro Asp Asp His Glu Pro
    210

<210> SEQ ID NO 21
<211> LENGTH: 195
<212> TYPE: PRT
<213> ORGANISM: Gossypium raimondii

<400> SEQUENCE: 21

Met Glu Lys Glu Glu Lys Lys Lys Met Glu Val Asp Ser Ala Pro
1               5                   10                  15

Ala Ala Ala Leu Glu Gly Phe Ser Pro Val Ser Thr Thr Arg Ile Phe
                20                  25                  30

Trp Asn Ser Arg Lys Arg Ser Ala Ser Gly Arg Asn Leu Asp Lys Val
            35                  40                  45

Thr Glu Glu Thr Ala Asn Val Thr Pro Thr Lys Gln Glu Glu Gln Thr
    50                  55                  60

Leu Asp Gln Asp Asn Thr Pro Asp Ser Ala Thr Ser Ser Glu Leu Ser
65                  70                  75                  80

Glu Arg Arg Lys Ala Leu Phe Glu Pro Leu Glu Pro Ile Lys Asn Ile
                85                  90                  95

Asn Gly Arg Arg Pro Ser Ala Glu Ser Leu Leu Pro Pro Asp Phe
                100                 105                 110
```

Asp Ala Ala Ser Tyr Pro Lys Gly Trp Leu Ile Gly Lys Arg Lys
            115                 120                 125

Leu Val Asn Val Asp Val Val Glu Ser Met Arg Arg Ile Ala Val Gln
    130                 135                 140

Glu Met Asn Arg Lys Asp Arg Glu Ile Asp Gly Leu Asn Glu Gln Leu
145                 150                 155                 160

Glu Glu Asp Ala Arg Cys Leu Glu His Leu Gln Leu Gln Leu Leu Gln
                165                 170                 175

Glu Lys Ser Lys Arg Ser Glu Val Glu Arg Glu Asn Ala Met Leu Gln
            180                 185                 190

Glu Gln Ser
        195

<210> SEQ ID NO 22
<211> LENGTH: 207
<212> TYPE: PRT
<213> ORGANISM: Foxtail millet

<400> SEQUENCE: 22

Met Glu Asp Pro Thr Pro Ala Asp Pro Pro Arg Ile Phe Trp Lys Ser
1               5                   10                  15

Arg Arg Ser Ala Asn Gly Arg Ser Leu Gln Gln Glu Pro Asp Lys Asp
                20                  25                  30

Ala Thr Glu Glu Val Asn Glu Gln Ala Gln Glu Ser Met Lys Ile
            35                  40                  45

Asp Asp Ala Thr Asp Thr Thr Ala Thr Ala Glu Asp Val Gln Pro Asp
        50                  55                  60

Pro Lys Ala Asn Leu Ser Glu Lys Arg Lys Ala Leu Phe Glu Pro Leu
65                  70                  75                  80

Glu Pro Ile Asn Gly Lys Arg Ser Ala Glu Met Leu Leu Pro Pro Pro
                85                  90                  95

Asp Phe Glu Pro Thr Ser Tyr Pro Lys Gly Trp Leu Val Gly Lys Lys
            100                 105                 110

Arg Lys Leu Val Asn Val Asp Val Val Glu Ser Met Arg Arg Ile Ala
        115                 120                 125

Val Gln Glu Met Asn Arg Lys Asp Arg Glu Ile Asn Gly Leu Asn Glu
    130                 135                 140

Gln Leu Glu Glu Asp Ser Arg Val Leu Glu Leu Leu Gln Lys Gln Leu
145                 150                 155                 160

Ala Asp Glu Arg Lys Lys Arg Ala Glu Ile Glu Lys Glu Asn Ser Met
                165                 170                 175

Leu His Glu Gln Val Ser Met Leu Met Asn Met Leu Asp Glu Asn Glu
            180                 185                 190

Gly Phe Asp Glu Glu Gly Glu Ala Pro Pro Asp Ser Phe Asp
        195                 200                 205

<210> SEQ ID NO 23
<211> LENGTH: 221
<212> TYPE: PRT
<213> ORGANISM: Hordeum vulgare vulgare

<400> SEQUENCE: 23

Met Glu Glu Pro Ser Met Val Asp Pro Pro Arg Ile Phe Trp Lys Ser
1               5                   10                  15

Arg Arg Arg Pro Ser Ser Ala Asn Gly Arg Ser Leu Gln Ala Gln Glu
                20                  25                  30

His Asn Asn Glu Ala Ala Ala Thr Glu Glu Ala Ala Ala Asp Asn Leu
            35                  40                  45

Pro Ala Gln Gly Glu Ala Met Lys Ile Asp Glu Val Asn Ala Ala Ser
 50                  55                  60

Thr Thr Thr Glu Asp Asp Ala His Gln Ala Asp Pro Met Ala Asn Leu
 65                  70                  75                  80

Ser Glu Lys Arg Lys Ala Leu Phe Glu Pro Leu Glu Pro Ile Asn Gly
                85                  90                  95

Lys Arg Ser Ser Ala Asp Met Leu Leu Pro Pro Asp Phe Glu Pro
            100                 105                 110

Ala Ser Tyr Pro Lys Gly Trp Leu Val Gly Lys Lys Arg Lys Leu Val
            115                 120                 125

Asn Val Asp Val Val Glu Ser Met Arg Arg Ile Ala Ile Leu Glu Met
130                 135                 140

Asn Arg Lys Asp Arg Glu Ile Gly Gly Leu Asn Glu Gln Leu Glu Glu
145                 150                 155                 160

Asp Ser Arg Val Leu Glu Leu Leu Gln Lys Gln Leu Thr Asp Glu Arg
                165                 170                 175

Arg Lys Arg Ser Glu Ile Glu Lys Glu Asn Ser Met Leu Gln Glu Gln
            180                 185                 190

Val Ser Met Leu Met Ser Met Leu Asp Glu Asn Glu Ala Phe Asp Glu
        195                 200                 205

Glu Gly Glu Glu Val Pro Pro Pro Asp Pro Ser Phe Asp
        210                 215                 220

<210> SEQ ID NO 24
<211> LENGTH: 35
<212> TYPE: DNA
<213> ORGANISM: Artificial Sequence
<220> FEATURE:
<223> OTHER INFORMATION: Synthetic sequence primer AttB1

<400> SEQUENCE: 24
aaaaagcagg cttcacaatg gagaaagggg ttgga                                    35

<210> SEQ ID NO 25
<211> LENGTH: 36
<212> TYPE: DNA
<213> ORGANISM: Artificial Sequence
<220> FEATURE:
<223> OTHER INFORMATION: Synthetic sequence primer AttB2

<400> SEQUENCE: 25
agaaagctgg gtttgatgag aactagctta gggttc                                   36

<210> SEQ ID NO 26
<211> LENGTH: 25
<212> TYPE: DNA
<213> ORGANISM: Artificial Sequence
<220> FEATURE:
<223> OTHER INFORMATION: Synthetic sequence primer AIP10 forward

<400> SEQUENCE: 26
ggagctgaag aaccctaagc tagtt                                               25

<210> SEQ ID NO 27
<211> LENGTH: 28
<212> TYPE: DNA
<213> ORGANISM: Artificial Sequence
<220> FEATURE:
<223> OTHER INFORMATION: Synthetic sequence primer AIP10 reverse

```
<400> SEQUENCE: 27
ggacgagaca aatctacaaa agaataaa                                          28

<210> SEQ ID NO 28
<211> LENGTH: 26
<212> TYPE: DNA
<213> ORGANISM: Artificial Sequence
<220> FEATURE:
<223> OTHER INFORMATION: Synthetic sequence primer UBI-14 forward

<400> SEQUENCE: 28
tcactggaaa gaccattact cttgaa                                            26

<210> SEQ ID NO 29
<211> LENGTH: 21
<212> TYPE: DNA
<213> ORGANISM: Artificial Sequence
<220> FEATURE:
<223> OTHER INFORMATION: Synthetic sequence primer UBI-14 reverse

<400> SEQUENCE: 29
agctgttttc cagcgaagat g                                                 21
```